(12) United States Patent
Tarasova et al.

(10) Patent No.: US 9,328,142 B2
(45) Date of Patent: May 3, 2016

(54) LIPOPEPTIDE INHIBITORS OF RAS ONCOPROTEINS

(75) Inventors: Nadya I. Tarasova, Frederick, MD (US); Sergey G. Tarasov, Frederick, MD (US); Vadim Gaponenko, Naperville, IL (US); Joseph Kates, Kirkland, WA (US); Alla Ivanova, Madison, CT (US); Michael C. Dean, Frederick, MD (US)

(73) Assignees: The United States of America, as represented by The Secretary, Department of Health and Human Services, Washington, DC (US); Joseph Robert Kates, Kirkland, WA (US); Yin Hwee Tan, Vancouver (CA); Vanderbilt University, Nashville, TN (US); The Board of Trustees of the University of Illinois, Urbana, IL (US)

( * ) Notice: Subject to any disclaimer, the term of this patent is extended or adjusted under 35 U.S.C. 154(b) by 0 days.

(21) Appl. No.: 14/119,596

(22) PCT Filed: May 25, 2012

(86) PCT No.: PCT/US2012/039623
§ 371 (c)(1),
(2), (4) Date: Jan. 30, 2014

(87) PCT Pub. No.: WO2012/162628
PCT Pub. Date: Nov. 29, 2012

(65) Prior Publication Data
US 2014/0135276 A1    May 15, 2014

Related U.S. Application Data

(60) Provisional application No. 61/489,919, filed on May 25, 2011.

(51) Int. Cl.
*C07K 7/08* (2006.01)
*C07K 7/06* (2006.01)
*C07K 14/82* (2006.01)

(52) U.S. Cl.
CPC ... *C07K 7/08* (2013.01); *C07K 7/06* (2013.01); *C07K 14/82* (2013.01)

(58) Field of Classification Search
CPC ............. C07K 14/82; C07K 7/06; C07K 7/08
See application file for complete search history.

(56) References Cited

U.S. PATENT DOCUMENTS

| 5,443,956 | A | 8/1995 | Carney |
| 5,962,243 | A | 10/1999 | Brown et al. |
| 6,159,947 | A | 12/2000 | Schweighoffer et al. |
| 6,696,280 | B2 | 2/2004 | Berlin et al. |
| 7,767,417 | B2 | 8/2010 | Philips et al. |

FOREIGN PATENT DOCUMENTS

| EP | 0108564 B1 | 5/1988 | |
| EP | 1867661 A1 | 12/2007 | |
| WO | WO 01/53458 A2 | 7/2001 | |
| WO | WO 2004/003170 A2 | 1/2004 | |
| WO | WO 2004014956 A1 * | 2/2004 | ............. A61K 39/09 |
| WO | WO 2010037395 A2 * | 4/2010 | ........... C07K 14/705 |

OTHER PUBLICATIONS

European Patent Office: International Search Report in International Patent Application No. PCT/US2012/039623 (May 15, 2014).
Adjei, *J. Thorac. Oncol.*, 3(6 Suppl. 2): S160-163 (2008).
Adler et al., *Cancer Chemother. Pharmacol.*, 62: 491-498 (2008).
Barnard et al., *Biochem., Biophys. Res. Commun.*, 247(1): 176-180 (1998).
Boissel et al., *Leukemia*, 20: 965-970 (2006).
Bowne et al., *Cancer Ther.*, 5: 331-346 (2007).
Friedman et al., *J. Protein Chem.*, 21: 361-366 (2002).
Graham et al., *Recent Results Cancer Res.*, 172: 125-153 (2007).
Kanovsky et al., *Cancer Chemother. Pharmacol.*, 52: 202-208 (2003).
Karnoub et al., *Nat. Rev. Mol. Cell Biol.*, 9: 517-531 (2008).
Lopez-Chavez et al., *Curr. Opin. Investig. Drugs*, 10: 1305-1314 (2009).
Pincus et al., *Cancer Investigation*, 18(1): 39-50 (2000).
Pincus, *Front. Biosci.*, 9: 3486-3509 (2004).
Quinlan et al., *Future Oncol.*, 5: 105-116 (2009).
Saxena et al., *Cancer Invest.*, 26: 948-955 (2008).
Schulz, *Int. J. Cancer*, 119: 1513-1518 (2006).
Yoo et al., *Arch. Pathol. Lab. Med.*, 124: 836-839 (2000).

* cited by examiner

*Primary Examiner* — James H Alstrum Acevedo
*Assistant Examiner* — Erinne Dabkowski
(74) *Attorney, Agent, or Firm* — Leydig, Voit & Mayer, LTD.

(57) ABSTRACT

The invention provides a peptide or peptidomimetic that is derived from or based upon the amino acid sequence of the C-terminal α-helix or hypervariable region (HVR) or a Ras protein, a nucleic acid encoding the peptide or peptidomimetic, and methods employing the same.

22 Claims, 17 Drawing Sheets

RASK HUMAN 1 (K-Ras-4a) = SEQ ID NO: 1
RASK HUMAN 2 (K-Ras-4b) = SEQ ID NO: 2
RASH HUMAN (H-Ras) = SEQ ID NO: 3
RASN HUMAN (N-Ras) = SEQ ID NO: 4

US 9,328,142 B2

LIPOPEPTIDE INHIBITORS OF RAS ONCOPROTEINS

CROSS-REFERENCE TO RELATED APPLICATIONS

This patent application is the U.S. national phase of International Patent Application No. PCT/US2012/039623, filed May 25, 2012, which claims the benefit of U.S. Provisional Patent Application No. 61/489,919, filed May 25, 2011, each of which is incorporated by reference in its entirety herein.

INCORPORATION-BY-REFERENCE OF MATERIAL SUBMITTED ELECTRONICALLY

Incorporated by reference in its entirety herein is a computer-readable nucleotide/amino acid sequence listing submitted concurrently herewith and identified as follows: One 36,424 Byte ASCII (Text) file named "715550ST25.TXT," dated Nov. 4, 2013.

Applicants request entry of the sequence listing submitted herewith into the specification.

BACKGROUND OF THE INVENTION

Ras proteins are small GTPases that act as signal transducers between cell surface receptors and several intracellular signaling cascades. These molecules regulate such essential cellular functions as cell survival, proliferation, motility, and cytoskeletal organization (see Karnoub et al., *Nat. Rev. Mol. Cell Biol.*, 9: 517-531 (2008)).

Ras proteins function as GDP/GTP-regulated binary switches in signal transduction cascades that can lead to cell growth, proliferation, differentiation, or survival. In its active form, Ras is bound to GTP. This causes a conformational change that allows it to interact and bind to several effector molecules, most notably the members of the Raf family, the RalGDS family, and Phosphoinositide 3-kinases (PI3 Kinase). Ras then cleaves GTP to GDP resulting in its inactivation. In its oncogenic, mutated state, Ras is unable to hydrolyze GTP to GDP, thus staying in an active state and activating numerous pathways.

The Ras superfamily has at least five major branches that include Ras, Rho, Ran, Arf/Sar, Rab. The four classical p21 Ras proteins are H-Ras (Harvey sarcoma viral oncogene), N-Ras (neuroblastoma oncogene), and the splice variants K-Ras4A and K-Ras4B (Kirsten sarcoma viral oncogene) (see Karnoub et al., supra). They are collectively referred to as Ras.

The p21 Ras proteins share 85% of sequence homology and activate very similar signaling pathways. However, recent studies clearly demonstrate that each Ras isoform functions in a unique, radically different way from the other Ras proteins in normal physiological processes as well as in pathogenesis (Quinlan et al., *Future Oncol.*, 5: 105-116 (2009)). According to Catalogue of Somatic Mutations in Cancer (www.sanger.ac.uk/genetics/CGP/cosmic/), K-Ras mutations were detected in 22.1% of analyzed human tumors, N-Ras in 8.2%, and H-Ras in 3.3%.

Mutations in cellular Ras have been found to be present in a large percentage of all human cancers, such as leukemias, colon cancers, and lung cancer (see Quinlan et al., supra, and Boissel et al., *Leukemia*, 20: 965-970 (2006)). More specifically, K-Ras mutations occur frequently in lung, pancreatic, and colon cancers, where as H-Ras mutations are prevalent in bladder, kidney, thyroid, and salivary gland cancers (see Shulz, *Int. J. Cancer*, 119: 1513-1518 (2006), and Yoo et al., *Arch. Pathol., Lab Med.*, 124: 836-839 (2000)), and N-Ras mutations are associated with myeloid malignancies, germ cell tumors, melanoma, hepatocellular carcinoma, and leukemia. Additionally, K-Ras mutation is predictive of response to EGFR antagonists therapy in colorectal cancer (see Lopez-Chavez et al., *Curr. Opin. Investig. Drugs*, 10: 1305-1314 (2009)).

Despite the central role of ras proteins in oncogenesis and wide-spread efforts to develop ras-directed anti-cancer therapeutics, no selective, specific inhibitor of the ras pathway is available for clinical use, and ras mutant cancers remain among the most refractory to available treatments (Adjei, *J. Thorac. Oncol.*, 3: S160-163 (2008); Graham et al., *Recent Results Cancer Res.*, 172: 125-153 (2007); and Saxena et al., *Cancer Invest.*, 26: 948-955 (2008)). Moreover, no inhibitors acting directly on ras oncogenes have been developed even for in vitro use. Consequently, ras proteins are considered to be non-druggable targets. Therefore, there is a desire to identify inhibitors of ras oncoproteins.

BRIEF SUMMARY OF THE INVENTION

The invention provides a peptide or peptidomimetic comprising the amino acid sequence comprising eight or more contiguous amino acids of the C-terminal α-helix of a Ras protein (e.g., eight or more contiguous amino acids of one of SEQ ID NOs: 66-68, or inverse thereof), wherein the peptide or peptidomimetic comprises a total of about 30 or fewer amino acids. In a related aspect, the invention provides a peptide or peptidomimetic comprising $X_1YTLVRX_2X_3RX_4X_5$ (SEQ ID NO: 5) or the inverse thereof, wherein the peptide or peptidomimetic comprises about 30 or fewer amino acids.

The invention also provides a peptide or peptidomimetic comprising five or more contiguous amino acids of the hypervariable region (HVR) of a Ras protein (e.g., five or more contiguous amino acids of one of SEQ ID NOs: 69-72, or inverse thereof), wherein the peptide or peptidomimetic comprises a total of about 30 or fewer amino acids. In a related aspect, the invention provides a peptide or peptidomimetic comprising the amino acid sequence $KTPGX_1VKIKK$ (SEQ ID NO: 6) or inverse thereof, the amino acid sequence KKSKTK (SEQ ID NO: 7) or the inverse thereof, the amino acid sequence $SGPGX_1X_2SX_3X_4$ (SEQ ID NO: 8) or the inverse thereof, or the amino acid sequence $GTQGX_1X_2GLP$ (SEQ ID NO: 9) or the inverse thereof, wherein the peptide or peptidomimetic comprises about 30 or fewer amino acids.

The invention further provides a method of inhibiting the activity of a Ras protein in a cell comprising introducing a peptide or peptidomimetic described herein into the cell, whereby the activity of the Ras protein is inhibited.

The invention also provides a method for inhibiting the growth or proliferation of a cancer cell comprising administering a peptide or peptidomimetic described herein to the cancer cell, whereupon the growth or proliferation of the cancer cell is inhibited.

In addition, the invention provides a method of treating cancer in a host comprising administering to the host a peptide or peptidomimetic described herein or nucleic acid encoding same, whereby the cancer is treated.

Related compounds, compositions, and methods also are provided, as will be apparent from the detailed description of the invention.

DETAILED DESCRIPTION OF THE INVENTION

Figure 1:
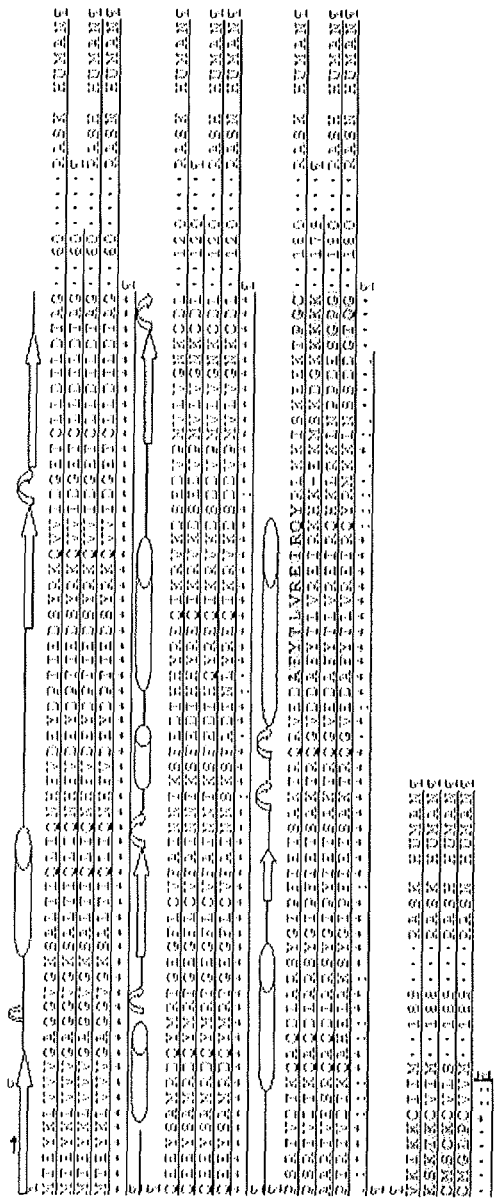
FIG. 1 depicts the primary structure alignment of four human Ras proteins with secondary structure elements shown above the sequences. The helix 6 and C-terminal hypervariable region (HVR) are shaded. Positions of the sequences that are conserved are marked with an asterisk. Positions of the sequences showing variation are marked with dots indicating the relative similarity between the residues that occupy a given position in the sequence. Two dots below a given position in the sequence indicate substitution by more closely related residues and one dot or no dots indicates substitution by less similar residues.

The invention provides a peptide or peptidomimetic that is derived from or based upon the amino acid sequence of the C-terminal α-helix of a Ras protein, particularly K-Ras-4a, K-Ras-4b, N-Ras, or H-Ras. The C-terminal α-helix of K-Ras-4a and N-Ras comprises the amino acid sequence of SEQ ID NO: 66. The C-terminal α-helixes of K-Ras-4b and H-Ras comprise the amino acid sequences of SEQ ID NO: 67 and SEQ ID NO: 68, respectively. In one aspect, the peptide or peptidomimetic comprises about eight or more (e.g., about nine or more, about ten or more, about eleven or more, or even about 12 or more) contiguous amino acids of the C-terminal α-helix of Ras or inverse thereof, provided that the peptide or peptidomimetic comprises a total of about 30 or fewer amino acids.

In a related aspect, the peptide or peptidomimetic comprises the amino acid sequence $X_1YTLVRX_2X_3RX_4X_5$ (SEQ ID NO: 5) or the inverse thereof, wherein the peptide or peptidomimetic comprises about 30 or fewer amino acids. Positions $X_1$-$X_5$ of SEQ ID NO: 5 can be any suitable amino acid. Desirably, $X_1$ is phenylalanine or tryptophan, $X_2$ is glutamic acid or glutamine, $X_3$ is isoleucine, valine, or lysine, $X_4$ is glutamine or lysine, and/or $X_5$ is tyrosine or histidine. Other amino acids also can be used, especially those having properties (e.g., size, polar or non-polar characteristics, charge, and or acid/base properties) similar to the amino acids provided above for any given position. More specific examples of a peptide or peptidomimetic comprising SEQ ID NO: 5 or the inverse thereof include, but are not limited to, those comprising any of SEQ ID NOs: 10-46, 66-68, and 75-84.

The invention provides a peptide or peptidomimetic that is derived from or based upon the amino acid sequence of the hypervariable region (HVR) of a Ras protein, particularly K-Ras-4a, K-Ras-4b, N-Ras, or H-Ras. The HVRs of K-Ras-4a, K-Ras-4b, H-Ras, and N-Ras comprise the amino acid sequences of SEQ ID NOs: 69-72, respectively. According to one aspect, the peptide or peptidomimetic comprises about five or more (e.g., about six or more, about seven or more, about eight or more, or about nine or more) contiguous amino acids of the HVR of Ras or inverse thereof, wherein the peptide or peptidomimetic comprises a total of about 30 or fewer amino acids.

In another aspect, the peptide or peptidomimetic comprises the amino acid sequence KTPGX$_1$VKIKK (SEQ ID NO: 6) or the inverse thereof, wherein the peptide or peptidomimetic comprises about 30 or fewer amino acids. $X_1$ of SEQ ID NO: 6 can be any suitable amino acid. Desirably, $X_1$ is serine, norleucine, or alanine. Other amino acids also can be used, especially those having similar properties to serine, norleucine, or alanine. More specific examples of a peptide or peptidomimetic comprising SEQ ID NO: 6 or the inverse thereof include, but are not limited to, those comprising any of SEQ ID NOs: 47-54 and 69.

Alternatively, the peptide or peptidomimetic comprises the amino acid sequence KKSKTK (SEQ ID NO: 7) or the inverse thereof, wherein the peptide or peptidomimetic comprises about 30 or fewer amino acids. Particular examples of a peptide or peptidomimetic comprising SEQ ID NO: 7 or the inverse thereof include, but are not limited to, those comprising any of SEQ ID NOs: 55-63 and 70.

In yet another embodiment, the peptide or peptidomimetic comprises the amino acid sequence SGPGX$_1$X$_2$SX$_3$X$_4$ (SEQ ID NO: 8) or the inverse thereof, wherein the peptide or peptidomimetic comprises about 30 or fewer amino acids. X$_1$-X$_4$ of SEQ ID NO: 8 can be any suitable amino acid. In one embodiment, X$_1$-X$_3$ are non-polar amino acids, and/or X$_4$ is a non-polar or basic amino acid. Desirably, X$_1$ is cysteine or norleucine, X$_2$ is methionine or norleucine, X$_3$ is cysteine or norleucine, and/or X$_4$ is lysine or norleucine. More specific examples of a peptide or peptidomimetic comprising SEQ ID NO: 8 or the inverse thereof include, but are not limited to, those comprising any of SEQ ID NOs: 64, 71, 85, or 86.

According to still another aspect, the peptide or peptidomimetic comprises the amino acid sequence GTQGX$_1$X$_2$GLP (SEQ ID NO: 9), wherein the peptide or peptidomimetic comprises about 30 or fewer amino acids. X$_1$ and X$_2$ can be any suitable amino acid. According to one embodiment, X$_1$ and/or X$_2$ is a non-polar amino acid. In another embodiment, X$_1$ is cysteine or norleucine, and/or X$_2$ is methionine or norleucine. Particular examples of a peptide or peptidomimetic comprising SEQ ID NO: 9 or the inverse thereof include, but are not limited to, SEQ ID NOs: 65 and 72.

Preferably, the peptide or peptidomimetic inhibits Ras activity. The term "Ras" is sometimes used herein to refer to the superfamily of Ras proteins collectively and individually, and is intended to encompass any such protein, especially H-Ras, N-Ras, K-Ras4A, and K-Ras4B. For the purposes of this invention, a peptide or peptidomimetic is considered to inhibit Ras activity if it inhibits any biological function of a Ras protein. Biological functions of Ras proteins include, for example, signal transduction activity. Thus, for instance, a peptide or peptidomimetic is considered to inhibit Ras activity if, in the presence of the peptide or peptidomimetic, the signal transduction activity of a Ras protein is reduced to any degree as compared to the signal transduction activity of the Ras protein in the absence of the peptide or peptidomimetic. Preferably, the peptide or peptidomimetic inhibits Ras activity to a degree sufficient to reduce the rate of cell growth of a cancer cell, reduce malignant transformation of a host, and/or induce cell death of a cancer cell. Suitable assays to test for such a reduction in the biological activity of Ras are known in the art, including cell growth and cytotoxicity assays, migration and invasion assays, phosphorylation/de-phosphorylation of Ras downstream targets, and gene regulation assays (e.g., luciferase reporter assay).

The invention is not limited with respect to any particular mechanism of action. The peptide or peptidomimetic may inhibit Ras by binding to Ras or its targets, thereby interfering with Ras signal transduction. Alternatively, or in addition, the peptide or peptidomimetic may inhibit the multimerization of Ras and/or inhibit Ras' membrane binding activity. Of course, the peptide or peptidomimetic may act by some other mechanism, such as by increasing the rate of Ras protein degradation or enhancing expression of small RNA molecules (miRNAs) that interfere with Ras transcription.

The inventive peptide or peptidomimetic can further comprise one or more (e.g., 2, 3, 4, 5, 6, 7, 8, 9, 10, 11, 12, 13, 14, or 15) flanking residues. The flanking residues should be chosen so as not to interfere with the ability of the peptide to inhibit Ras activity. Guidance for the selection of such residues is provided by the relevant sequence of the C-terminal α-helix or HVR of Ras itself. For instance, one can choose residues for use in the peptide that are identical to, or have properties similar to, the residues at the corresponding positions of a given Ras protein (preferably a human Ras protein). The peptide or peptidomimetic can, for example, be a fragment of a Ras protein or have an amino acid sequence of a fragment of a Ras protein or the inverse sequence thereof.

Variant sequences other than those specifically mentioned herein are contemplated, which comprise significant sequence identity (e.g., 80%, 85%, 90%, 95%, 98%, or 99% sequence identity) to the amino acid sequence of the C-terminal α-helix (e.g., SEQ ID NOs: 66-68) or HVR (e.g., SEQ ID NOs: 69-72) or fragment thereof, provided that such variants retain the ability to inhibit Ras activity. Such variants can comprise one or more (e.g., 2, 3, 4, or 5) amino acid substitutions, deletions, or insertions as compared to the parent amino acid sequence. Conservative amino acid substitutions are known in the art, and include amino acid substitutions in which one amino acid having certain physical and/or chemical properties is exchanged for another amino acid that has the same or similar chemical or physical properties. For instance, the conservative amino acid substitution can be an acidic amino acid substituted for another acidic amino acid (e.g., Asp or Glu), an amino acid with a nonpolar side chain substituted for another amino acid with a nonpolar side chain (e.g., Ala, Gly, Val, Ile, Leu, Met, Phe, Pro, Trp, Val, etc.), a basic amino acid substituted for another basic amino acid (Lys, Arg, etc.), an amino acid with a polar side chain substituted for another amino acid with a polar side chain (Asn, Cys, Gln, Ser, Thr, Tyr, etc.), etc.

The peptide or peptidomimetic also can comprise synthetic, non-naturally occurring amino acids. Such synthetic amino acids include, for example, aminocyclohexane carboxylic acid, norleucine, α-amino n-decanoic acid, homoserine, S-acetylaminomethyl-cysteine, trans-3- and trans-4-hydroxyproline, 4-aminophenylalanine, 4-nitrophenylalanine, 4-chlorophenylalanine, 4-carboxyphenylalanine, β-phenylserine β-hydroxyphenylalanine, phenylglycine, α-naphthylalanine, cyclohexylalanine, cyclohexylglycine, indoline-2-carboxylic acid, 1,2,3,4-tetrahydroisoquinoline-3-carboxylic acid, aminomalonic acid, aminomalonic acid monoamide, N'-benzyl-N'-methyl-lysine, N',N'-dibenzyl-lysine, 6-hydroxylysine, ornithine, α-aminocyclopentane carboxylic acid, α-aminocyclohexane carboxylic acid, α-aminocycloheptane carboxylic acid, α-(2-amino-2-norbornane)-carboxylic acid, α,γ-diaminobutyric acid, α,β-diaminopropionic acid, homophenylalanine, and α-tert-butylglycine. The properties of such synthetic amino acids are well-documented. Any natural amino acid of one or more of the sequences discussed herein can be substituted with a synthetic amino acid having similar properties.

The term "peptidomimetic" as used herein refers to a compound that comprises the same general structure of a corresponding polypeptide, but which includes modifications that increase its stability or biological function. For instance, the peptidomimetic can be a "retro" or "reverso" analogue of a given peptide, which means that the peptidomimetic comprises the reverse sequence of the peptide. In addition, or instead, the peptidomimetic can comprise one or more amino acids in a "D" configuration (e.g., D-amino acids), providing an "inverso" analogue. Peptides comprising both a reverse sequence and D-amino acids are referred to as "retro-inverso" peptides. Peptidomimetics also include peptoids, wherein the sidechain of each amino acid is appended to the nitrogen atom of the amino acid as opposed to the alpha carbon. Peptoids can, thus, be considered as N-substituted glycines which have repeating units of the general structure of $NRCH_2CO$ and which have the same or substantially the same amino acid sequence as the corresponding polypeptide. In this respect, the peptide or peptidomimetic can comprise any of the sequences described herein in reverse order.

Smaller peptides and peptidomimetics are believed to be advantageous for inhibiting Ras function and to facilitate entry into a cell. Thus, the peptide or peptidomimetic preferably comprises about 30 or fewer amino acids, such as about 25 or fewer amino acids, about 20 or fewer amino acids, or about 15 or fewer amino acids or even about 12 or fewer amino acids. Generally, however, the peptide or peptidomimetic will comprise about 8 or more amino acids, such as about 10 or more amino acids, about 12 or more amino acids, or about 15 or more amino acids.

The peptide or peptidomimetic can comprise, consist essentially of, or consist of, any of foregoing sequences or variants thereof. The peptide or peptidomimetic consists essentially of the foregoing sequences if it does not comprise other elements, such as other amino acid sequences, that prevent the peptide from inhibiting Ras activity.

The peptide or peptidomimetic coupled to a cell penetrating motif or other moiety so as to more efficiently facilitate the delivery of the peptide to the interior of a cell, anchor the peptide to the cell membrane of a cell, and/or promote folding of the peptide. Thus, the peptide or peptidomimetic can be provided as part of a composition comprising the peptide and cell penetrating motif or other moiety. Any of various cell penetrating motifs and or other moieties useful for these purposes can be used. By way of illustration, suitable cell penetrating motifs and other relevant moieties (e.g., cell-membrane anchoring moieties) include lipids and fatty acids, peptide transduction domains (e.g., HIV-TAT, HSV Transcription Factor (VP22), and penetratin), and other types of carrier molecules (e.g., Pep-1).

According to one aspect of the invention, the cell penetrating motif or other moiety comprises a fatty acid or lipid molecule. The fatty acid or lipid molecule can be, for example, a palmitoyl group, farnesyl group (e.g., farnesyl diphosphate), a geranylgeranyl group (e.g., geranylgeranyl diphosphate), a phospholipid group, glycophosphatidylinositol, phosphatidylserine, phosphatidylethanolamine, sphingomyelin, phosphatidylcholine, cardiolipin, phosphatidylinositol, phosphatidic acid, lysophosphoglyceride, a cholesterol group, and the like. Preferably, the fatty acid molecule is a $C_1$ to $C_{24}$ fatty acid or $C_6$ to $C_{14}$ fatty acid. Desirably, the fatty acid comprises three or more, four or more, five or more, six or more, seven or more, eight or more, nine or more or ten or more carbon atoms. Typically, the fatty acid will comprise 22 or fewer, 20 or fewer, 18 or fewer, or 16 or fewer carbon atoms. Specific examples of fatty acids include, without limitation, lauric acid, myristic acid, stearic acid, oleic acid, linoleic acid, α-linoleic acid, linolenic acid, arachidonic acid, timnodonic acid, docosohexenoic acid, erucic acid, arachidic acid, behenic acid, aminoisobutiric acid (Aib), caprylic acid (Cap), and octanoic acid (Oct).

The fatty acid or lipid molecule can be attached to any suitable part of the peptide or peptidomimetic. In a preferred embodiment of the invention, the fatty acid or lipid molecule is attached at the amino (N-) terminus, the carboxyl (C-) terminus, or both the N- and C-termini of the peptide or peptidomimetic. Typically, the fatty acid or lipid molecule is attached via an amide or ester linkage. When the fatty acid or lipid molecule is attached at the C-terminus of the polypeptide or peptidomimetic, the fatty acid or lipid molecule preferably is modified, e.g., to include an amino group such as $NH_2(CH_2)_nCOOH$ or $CH_3(CH_2)_mCH(NH_2)COOH$, wherein each of n and m is, independently, 1 to 24, preferably 6 to 14. The fatty acid or lipid residue can advantageously be attached to a terminal lysine in the epsilon (ε) position.

According to another aspect of the invention, the cell penetrating motif is a peptide transduction domain (also known as protein transduction domains or PTDs). PTDs typically are fused to the Ras-inhibitory peptide or peptidomimetic. Thus, the peptide or peptidomimetic can be a fusion protein comprising the peptide or peptidomimetic and a PTD. Often, the fusion protein is cleaved inside of a cell to remove the cell penetrating motif.

The peptide or peptidomimetic can further comprise linking residues disposed between the amino acid sequence derived from or based upon the C-terminal α-helix or HVR of Ras and the cell penetrating motif or other moiety. Illustrative examples of such linking residues include K, KK, RK, RQ, KQ, RQI, KQI, RQIK (SEQ ID NO: 73), and KQIK (SEQ ID NO: 74).

The peptide or peptidomimetic can be prepared by any method, such as by synthesizing the peptide or peptidomimetic, or by expressing a nucleic acid encoding an appropriate amino acid sequence in a cell and harvesting the peptide from the cell. Of course, a combination of such methods also can be used. Methods of de novo synthesizing peptides and peptidomimetics, and methods of recombinantly producing peptides and peptidomimetics are known in the art (see, e.g., Chan et al., *Fmoc Solid Phase Peptide Synthesis*, Oxford University Press, Oxford, United Kingdom, 2005; *Peptide and Protein Drug Analysis*, ed. Reid, R., Marcel Dekker, Inc., 2000; *Epitope Mapping*, ed. Westwood et al., Oxford University Press, Oxford, United Kingdom, 2000; Sambrook et al., *Molecular Cloning: A Laboratory Manual*, 3$^{rd}$ ed., Cold Spring Harbor Press, Cold Spring Harbor, N.Y. 2001; and Ausubel et al., *Current Protocols in Molecular Biology*, Greene Publishing Associates and John Wiley & Sons, NY, 1994).

The invention also provides a nucleic acid encoding the amino acid sequence of the peptide or peptidomimetic. The nucleic acid can comprise DNA or RNA, and can be single or double stranded. Furthermore, the nucleic acid can comprise nucleotide analogues or derivatives (e.g., inosine or phosphorothioate nucleotides and the like). The nucleic acid can encode the amino acid sequence of the peptide or peptidomimetic alone, or as part of a fusion protein comprising such sequence and a cell penetrating motif, as described herein. The nucleic acid encoding the amino acid sequence of the peptide or peptidomimetic can be provided as part of a construct comprising the nucleic acid and elements that enable delivery of the nucleic acid to a cell, and/or expression of the nucleic acid in a cell. Such elements include, for example, expression vectors and transcription and/or translation sequences. Suitable vectors, transcription/translation sequences, and other elements, as well as methods of preparing such nucleic acids and constructs, are known in the art (e.g., Sambrook et al., supra; and Ausubel et al., supra). Accordingly, a recombinant vector comprising the nucleic acid encoding the amino acid sequence of the peptide or peptidomimetic also is encompassed by the invention.

The invention further provides an antibody to the peptide or peptidomimetic, or an antigen binding fragment or portion thereof (e.g., Fab, F(ab')$_2$, dsFv, sFv, diabodies, and triabodies). The antibody can be monoclonal or polyclonal, and of any isotype, e.g., IgA, IgD, IgE, IgG, IgM, etc. The antibody can be a naturally-occurring antibody, e.g., an antibody isolated and/or purified from a mammal, e.g., mouse, rabbit, goat, horse, chicken, hamster, human, etc. Alternatively, the antibody can be a synthetic or genetically-engineered antibody, e.g., a humanized antibody or a chimeric antibody. The antibody can be in monomeric or polymeric form. The antibody, or antigen binding portion thereof, can be modified to comprise a detectable label, such as, for instance, a radioisotope, a fluorophore (e.g., fluorescein isothiocyanate (FITC), phycoerythrin (PE)), an enzyme (e.g., alkaline phosphatase, horseradish peroxidase), or element particles (e.g., gold particles). Such antibodies can be used for any purpose, such as to facilitate the detection or purification of a peptide or peptidomimetic described herein. Suitable methods of making antibodies are known in the art, including standard hybridoma methods, EBV-hybridoma methods, bacteriophage vector expression systems, and phage-display systems (see, e.g., Köhler and Milstein, *Eur. J. Immunol.*, 5, 511-519 (1976); Harlow and Lane (eds.), *Antibodies: A Laboratory Manual*, CSH Press (1988); C. A. Janeway et al. (eds.), *Immunobiology*, 5$^{th}$ Ed., Garland Publishing, New York, N.Y. (2001); Haskard and Archer, *J. Immunol. Methods*, 74(2), 361-67 (1984); Roder et al., *Methods Enzymol.*, 121, 140-67 (1986); Huse et al., *Science*, 246, 1275-81 (1989); Sambrook et al., supra; Ausubel et al., supra; and Knappik et al., *J. Mol. Biol.* 296: 57-86 (2000)).

The peptide or peptidomimetic, nucleic acid, or antibody can be isolated. The term "isolated" as used herein encompasses compounds or compositions that have been removed from a biological environment (e.g., a cell, tissue, culture medium, body fluid, etc.), or otherwise increased in purity to any degree (e.g., isolated from a synthesis medium). Isolated compounds and compositions, thus, can be synthetic or naturally produced.

A cell comprising the peptide or peptidomimetic, nucleic acid encoding the amino acid sequence of the peptide or peptidomimetic, or recombinant vector comprising the nucleic acid also is provided herein. Such a cell includes, for example, a cell engineered to express a nucleic acid encoding the amino acid sequence of the peptide or peptidomimetic. Suitable cells include prokaryotic and eukaryotic cells, e.g., mammalian cells, yeast, fungi, and bacteria (such as *E. coli*). The cell can be in vitro, as is useful for research or for production of the peptide or peptidomimetic, or the cell can be in vivo, for example, in a transgenic mammal that expresses the peptide.

The peptide or peptidomimetic can be used for any purpose, but is especially useful for inhibiting Ras activity in a cell. Thus, provided herein is a method of inhibiting Ras activity in a cell, which method comprises administering a peptide or peptidomimetic described herein to a cell in an amount sufficient to inhibit Ras activity.

The peptide or peptidomimetic can be administered to the cell by any method. For example, the peptide or peptidomimetic can be administered to a cell by contacting the cell with the peptide or peptidomimetic, typically in conjunction with a reagent or other technique (e.g., microinjection or electroporation) that facilitates cellular uptake. Alternatively, and preferably, the peptide or peptidomimetic is administered by contacting the cell with a composition comprising the peptide or peptidomimetic and a cell penetrating motif, as discussed herein. The peptide or peptidomimetic additionally or alternatively can be encapsulated in nanoparticles (e.g., using the methods described in International Patent Application Publication 2008/058125) prior to administration to the cell.

The peptide or peptidomimetic also can be administered by introducing a nucleic acid encoding the amino acid sequence of the peptide into the cell such that the cell expresses a peptide comprising the amino acid sequence. The nucleic acid encoding the peptide can be introduced into the cell by any of various techniques, such as by contacting the cell with the nucleic acid or a composition comprising the nucleic acid as part of a construct, as described herein, that enables the delivery and expression of the nucleic acid. Specific protocols for introducing and expressing nucleic acids in cells are known in the art (see, e.g., Sambrook et al. (eds.), supra; and Ausubel et al., supra).

The peptide, peptidomimetic, or nucleic acid can be administered to a cell in vivo by administering the peptide, peptidomimetic, nucleic acid encoding the peptide or peptidomimetic, or recombinant vector comprising the nucleic acid. The host can be any host, such as a mammal, preferably a human. Suitable methods of administering peptides, peptidomimetics, and nucleic acids to hosts are known in the art, and discussed in greater detail in connection with the pharmaceutical composition comprising such compounds, below.

The cell can be any type of cell that comprises Ras. Preferably, the cell is of a type that is related to a disease or condition mediated by Ras activity. For example, the cell can be an engineered cell that is designed to mimic a condition or disease associated with Ras activity, or the cell can be a cell of a patient afflicted with a disease or condition associated with Ras activity. Diseases mediated by Ras include diseases characterized by Ras overexpression or overactivity. Cancer cells are one example of a cell type that can be used. The cell can be in vitro or in vivo in any type of animal, such as a mammal, preferably a human.

The method of inhibiting Ras activity in a cell can be used for any purpose, such as for the research, treatment, or prevention of diseases or conditions mediated by Ras. Ras activity has been linked to a large variety of cancers. Thus, according to one aspect of the method of the invention, the peptide or peptidomimetic is administered to a cancer cell, in vitro or in vivo, and administration of the peptide or peptidomimetic to the cancer cell inhibits the growth or survival of the cancer cell.

The cancer cell can be a cell of any type of cancer, in vitro or in vivo, particularly those associated with Ras activity, such as those associated with Ras overexpression, up-regulation of Ras, and/or increased activation of Ras (e.g., constitutive activation of Ras). Non-limiting examples of specific types of cancers include cancer of the head and neck, eye, skin, mouth, throat, esophagus, chest, bone, lung, colon, sigmoid, rectum, stomach, prostate, breast, ovaries, kidney, liver, pancreas, brain, intestine, heart or adrenals. More particularly, cancers include solid tumor, sarcoma, carcinomas, fibrosarcoma, myxosarcoma, liposarcoma, chondrosarcoma, osteogenic sarcoma, chordoma, angiosarcoma, endotheliosarcoma, lymphangiosarcoma, lymphangioendothelio sarcoma, synovioma, mesothelioma, Ewing's tumor, leiomyosarcoma, rhabdomyosarcoma, colon carcinoma, pancreatic cancer, breast cancer, ovarian cancer, prostate cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, bile duct carcinoma, choriocarcinoma, seminoma, embryonal carcinoma, Wilms' tumor, cervical cancer, testicular tumor, lung carcinoma, small cell lung carcinoma, bladder carcinoma, epithelial carcinoma, glioma, astrocytoma, medulloblastoma, craniopharyngioma, ependymoma, Kaposi's sarcoma, pinealoma, hemangioblastoma, acoustic neuroma, oligodendroglioma, menangioma, melanoma, neuroblastoma, retinoblastoma, a blood-born tumor, acute lymphoblastic leukemia, acute lymphoblastic B-cell leukemia, acute lymphoblastic T-cell leukemia, acute myeloblastic leukemia, acute promyelocytic leukemia, acute monoblastic leukemia, acute erythroleukemic leukemia, acute megakaryoblastic leukemia, acute myelomonocytic leukemia, acutenonlymphocytic leukemia, acute undifferentiated leukemia, chronic myelocytic leukemia, chronic lymphocytic leukemia, hairy cell leukemia, or multiple myeloma. See, e.g., *Harrison's Principles of Internal Medicine*, Eugene Braunwald et al., eds., pp. 491 762 (15th ed. 2001). The methods of the invention are believed to be especially useful for the treatment of leukemia, pancreatic cancer, colon (colorectal) cancer, ovarian cancer, lung cancer, bladder cancer, cancer of the salivary gland, myeloid malignancies, germ cell tumors, and melanoma, as well as any other cancer known to be responsive to Ras inhibitors.

Ras activity also has been linked to other diseases, including Costello syndrome, Noonan syndrome, and autoimmune diseases, such as Alopecia areata, Ankylosing spondylitis, Crohns Disease, Graves' disease, Dermatomyositis, Diabetes mellitus type 1, Goodpasture's syndrome, Guillain-Barré syndrome (GBS), Hashimoto's disease, Idiopathic thrombocytopenic purpura, Lupus erythematosus, Mixed Connective Tissue Disease, Multiple Sclerosis, Myasthenia gravis, Narcolepsy, Pemphigus vulgaris, Pernicious anaemia, Psoriasis, Psoriatic Arthritis, Polymyositis, Primary biliary cirrhosis, Relapsing polychondritis, Rheumatoid arthritis, Sjögren's syndrome, Temporal arteritis (also known as "giant cell arteritis"), Ulcerative Colitis (one of two types of idiopathic inflammatory bowel disease "IBD"), Vasculitis, and Wegener's granulomatosis. Thus, the methods of the invention are believed to be useful for the treatment of such diseases, as well.

Peptides and peptidomimetics, as described herein, include salts, esters, alkylated (e.g., methylated), and acetylated peptides. Any one or more of the compounds or compositions of the invention described herein (e.g., peptide or peptidomimetic, nucleic acid, antibody, or cell) can be formulated as a pharmaceutical composition, comprising a compound of the invention and a pharmaceutically acceptable carrier. Furthermore, the compounds or compositions of the invention can be used in the methods described herein alone or as part of a pharmaceutical formulation.

The pharmaceutical composition can comprise more than one compound or composition of the invention. Alternatively, or in addition, the pharmaceutical composition can comprise one or more other pharmaceutically active agents or drugs. Examples of such other pharmaceutically active agents or drugs that may be suitable for use in the pharmaceutical composition include anticancer agents. Suitable anticancer agents include, without limitation, alkylating agents; nitrogen mustards; folate antagonists; purine antagonists; pyrimidine antagoinists; spindle poisons; topoisomerase inhibitors; apoptosis inducing agents; angiogenesis inhibitors; podophyllotoxins; nitrosoureas; cisplatin; carboplatin; interferon; asparginase; tamoxifen; leuprolide; flutamide; megestrol; mitomycin; bleomycin; doxorubicin; irinotecan; and taxol, geldanamycin (e.g., 17-AAG), and various anti-cancer peptides and antibodies.

The carrier can be any of those conventionally used and is limited only by physio-chemical considerations, such as solubility and lack of reactivity with the active compound(s), and by the route of administration. The pharmaceutically acceptable carriers described herein, for example, vehicles, adjuvants, excipients, and diluents, are well-known to those skilled in the art and are readily available to the public. It is preferred that the pharmaceutically acceptable carrier be one which is chemically inert to the active agent(s) and one which has no detrimental side effects or toxicity under the conditions of use.

The choice of carrier will be determined in part by the particular compound or composition of the invention and other active agents or drugs used, as well as by the particular method used to administer the compound and/or inhibitor. Accordingly, there are a variety of suitable formulations of the pharmaceutical composition of the present inventive methods. The following formulations for oral, aerosol, parenteral, subcutaneous, intravenous, intramuscular, interperitoneal, rectal, and vaginal administration are exemplary and are in no way limiting. One skilled in the art will appreciate that these routes of administering the compound of the invention are known, and, although more than one route can be used to administer a particular compound, a particular route can provide a more immediate and more effective response than another route.

Injectable formulations are among those formulations that are preferred in accordance with the present invention. The requirements for effective pharmaceutical carriers for injectable compositions are well-known to those of ordinary skill in the art (See, e.g., *Pharmaceutics and Pharmacy Practice*, J.B. Lippincott Company, Philadelphia, Pa., Banker and Chalmers, eds., pages 238-250 (1982), and *ASHP Handbook on Injectable Drugs*, Toissel, 4th ed., pages 622-630 (1986)).

Topical formulations are well-known to those of skill in the art. Such formulations are particularly suitable in the context of the present invention for application to the skin.

Formulations suitable for oral administration can consist of (a) liquid solutions, such as an effective amount of the inhibitor dissolved in diluents, such as water, saline, or orange juice; (b) capsules, sachets, tablets, lozenges, and troches, each containing a predetermined amount of the active ingredient, as solids or granules; (c) powders; (d) suspensions in an appropriate liquid; and (e) suitable emulsions. Liquid formulations may include diluents, such as water and alcohols, for example, ethanol, benzyl alcohol, and the polyethylene alcohols, either with or without the addition of a pharmaceutically acceptable surfactant. Capsule forms can be of the ordinary hard- or soft-shelled gelatin type containing, for example, surfactants, lubricants, and inert fillers, such as lactose, sucrose, calcium phosphate, and corn starch. Tablet forms can include one or more of lactose, sucrose, mannitol, corn starch, potato starch, alginic acid, microcrystalline cellulose, acacia, gelatin, guar gum, colloidal silicon dioxide, croscarmellose sodium, talc, magnesium stearate, calcium stearate, zinc stearate, stearic acid, and other excipients, colorants, diluents, buffering agents, disintegrating agents, moistening agents, preservatives, flavoring agents, and pharmacologically compatible excipients. Lozenge forms can comprise the active ingredient in a flavor, usually sucrose and acacia or tragacanth, as well as pastilles comprising the active ingredient in an inert base, such as gelatin and glycerin, or sucrose and acacia, emulsions, gels, and the like containing, in addition to the active ingredient, such excipients as are known in the art.

The compounds and compositions of the invention, alone or in combination with other suitable components, can be made into aerosol formulations to be administered via inhalation. These aerosol formulations can be placed into pressurized acceptable propellants, such as dichlorodifluoromethane, propane, nitrogen, and the like. They also may be formulated as pharmaceuticals for non-pressured preparations, such as in a nebulizer or an atomizer. Such spray formulations also may be used to spray mucosa.

Formulations suitable for parenteral administration include aqueous and non-aqueous, isotonic sterile injection solutions, which can contain anti-oxidants, buffers, bacteriostats, and solutes that render the formulation isotonic with the blood of the intended recipient, and aqueous and non-aqueous sterile suspensions that can include suspending agents, solubilizers, thickening agents, stabilizers, and preservatives. The compounds and compositions of the invention can be administered in a physiologically acceptable diluent in a pharmaceutical carrier, such as a sterile liquid or mixture of liquids, including water, saline, aqueous dextrose and related sugar solutions, an alcohol, such as ethanol, isopropanol, or hexadecyl alcohol, glycols, such as propylene glycol or poly(ethylene glycol), dimethylsulfoxide, glycerol ketals, such as 2,2-dimethyl-1,3-dioxolane-4-methanol, ethers, such as poly(ethyleneglycol) 400, an oil, a fatty acid, a fatty acid ester or glyceride, or an acetylated fatty acid glyceride with or without the addition of a pharmaceutically acceptable surfactant, such as a soap or a detergent, suspending agent, such as pectin, carbomers, methylcellulose, hydroxypropylmethylcellulose, or carboxymethylcellulose, or emulsifying agents and other pharmaceutical adjuvants.

Oils, which can be used in parenteral formulations include petroleum, animal, vegetable, or synthetic oils. Specific examples of oils include peanut, soybean, sesame, cottonseed, corn, olive, petrolatum, and mineral. Suitable fatty acids for use in parenteral formulations include oleic acid, stearic acid, and isostearic acid. Ethyl oleate and isopropyl myristate are examples of suitable fatty acid esters.

Suitable soaps for use in parenteral formulations include fatty alkali metal, ammonium, and triethanolamine salts, and suitable detergents include (a) cationic detergents such as, for example, dimethyl dialkyl ammonium halides, and alkyl pyridinium halides, (b) anionic detergents such as, for example, alkyl, aryl, and olefin sulfonates, alkyl, olefin, ether, and monoglyceride sulfates, and sulfosuccinates, (c) nonionic detergents such as, for example, fatty amine oxides, fatty acid alkanolamides, and polyoxyethylenepolypropylene copolymers, (d) amphoteric detergents such as, for example, alkyl-b-aminopropionates, and 2-alkyl-imidazoline quaternary ammonium salts, and (e) mixtures thereof.

Preservatives and buffers may be used. In order to minimize or eliminate irritation at the site of injection, such compositions may contain one or more nonionic surfactants having a hydrophile-lipophile balance (HLB) of from about 12 to about 17. The quantity of surfactant in such formulations will typically range from about 5% to about 15% by weight. Suitable surfactants include polyethylene sorbitan fatty acid esters, such as sorbitan monooleate and the high molecular weight adducts of ethylene oxide with a hydrophobic base, formed by the condensation of propylene oxide with propylene glycol. The parenteral formulations can be presented in unit-dose or multi-dose sealed containers, such as ampoules and vials, and can be stored in a freeze-dried (lyophilized) condition requiring only the addition of the sterile liquid excipient, for example, water, for injections, immediately prior to use. Extemporaneous injection solutions and suspensions can be prepared from sterile powders, granules, and tablets of the kind previously described.

Additionally, the compounds of the invention, or compositions comprising such compounds, can be made into suppositories by mixing with a variety of bases, such as emulsifying bases or water-soluble bases. Formulations suitable for vaginal administration can be presented as pessaries, tampons, creams, gels, pastes, foams, or spray formulas containing, in addition to the active ingredient, such carriers as are known in the art to be appropriate.

The following examples further illustrate the invention but, of course, should not be construed as in any way limiting its scope.

EXAMPLES

Except otherwise stated, the peptides referenced in the following examples were prepared and analyzed as follows:
Peptide Synthesis and Purification The peptides were synthesized on a 433A Peptide Synthesizer (Applied Biosystems) using Fmoc chemistry. The peptides were cleaved from the resin and deprotected with a mixture of 90.0% (v/v) trifluoroacetic acid (TFA) with 2.5% water, 2.5% triisopropyl-silane, and 5% thioanisol. The resin and deprotection mixture were pre-chilled to −5° C. and reacted for 15 minutes at −5° C. with stirring. The reaction was allowed to continue at room temperature for 1 hour and 45 minutes. The resin was filtered off and the product was precipitated with cold diethyl ether. The resin was washed with neat TFA. Peptide suspended in diethyl ether was centrifuged at −20° C. and the precipitate was washed with diethyl ether four more times and left to dry in a vacuum overnight. The dried crude peptide was dissolved in DMSO and purified on a preparative (25 mm×250 mm) Atlantis C18 reverse phase column (Agilent Technologies) in a 90 minute gradient of 0.1% (v/v) trifluoroacetic acid in water and 0.1% trifluoroacetic acid in acetonitrile with a 10 mL/min flow rate. The fractions containing peptides were analyzed on Agilent 1100 LC/MS spectrometer with the use of a Zorbax 300SB-C3 Poroshell column and a gradient of 5% acetic acid in water and acetonitrile. Fractions that were more than 95% pure were combined and freeze dried. Resin preloaded with α-Fmoc-ε-palmytoil-Lys was prepared as described in Remsberg et al., *J. Med. Chem.*, 50: 4534-4538 (2007).
Cell Toxicity Assay MCF-7 (breast cancer), T47D (breast cancer), Colo 205 (colon cancer), JM-1 (rat hepatoma), Sk Mel-2 (melanoma), PLC (human hepatoma), and HepG2 (human hepatoma) were obtained from American Type Cell Culture Collection. MCF-7 cells were grown in RPMI medium supplemented with 10% Fetal Bovine Serum. The remaining cell lines were grown in DMEM medium supplemented with 10% Fetal Bovine Serum. For the assay, cells were seeded into 96 well plates in medium containing 1% Fetal Bovine Serum and 100 µL of a cell suspension containing 5000 cells per well were used for each well. Cell growth was evaluated utilizing MTT ((3-(4,5-Dimethylthiazol-2-yl)-2,5-diphenyltetrazolium). The absorbance of the wells at 544 nm was determined by a FLUOstar/POLARstar Galaxy (BMG Lab Technologies GmbH) microplate reader.
Cell Invasion Assays Cell invasion assays were performed using the BD Biocoat Matrigel Invasion Chambers in accordance with the manufacturer's protocol. Cells ($1 \times 10^5$/mL) were seeded onto 12-well cell culture chamber using inserts with 8 µm pore size polycarbonate membrane over a thin layer of Matrigel Basement Membrane Matrix without phenol red (BD Biosciences) diluted at 1:100 in PBS. Following incubation of the plates for 48 hours at 37° C., cells that invaded through the Matrigel and migrated to the lower surface of the membrane were stained with Giemsa solution, counted under the microscope in at least 10 different fields, and photographed. Three wells were examined for each condition and cell type, and the experiments were repeated in triplicate.

Example 1

This example demonstrates the identification of analogs of the C-terminal α-helix of Ras.

The design of inhibitors was based on available x-ray structures of K-Ras and H-Ras proteins. The structures have suggested that the C-terminal α-helix of the proteins (helix 6 in K-Ras) occupies central position in the protein, is involved in multiple intramolecular interactions, and, thus, is likely to play a critical role in both structure stabilization and structural rearrangements during signaling events.

A library of synthetic peptide analogs of helix 6 was constructed. For structural stabilization of protein fragments and membrane anchoring, all peptide analogs were equipped with palmitate residues (see Table 1). The sequences of the peptides are presented in Table 1, wherein amino acid substitutions in the native sequences are in bold.

TABLE 1

Structure-activity relationships in derivatives of the C-terminal α-helix of K-Ras.

| Compound | SEQ ID NO | Structure | $GI_{50}$, nM |
|---|---|---|---|
| kR-H6-1 | 10 | Pal-RYQRIERVLTYFADEV (all D) | 1350 |
| kR-H6-2 | 11 | Pal-LRYQRIERVLTYFADEV (all D) | 300 |
| kR-H6-3 | 12 | e-Pal-KRYQRIERVLTYFADEV (all D) | >5000 |
| kR-H6-4 | 13 | Pal-KVEDAFYTLVREIRQYR | >5000 |
| kR-H6-5 | 14 | Ac-Doa-VEDAFYTLVREIRQYR | 3300 |
| kR-H6-6 | 15 | Pal-e-KAFYTLVREIRQYR | 250 |
| kR-H6-7 | 16 | Ac-VEDAFYTLVREIRQYRK (e-Pal) | 2700 |
| kR-H6-8 | 17 | Ac-AFYTLVREIRQYRK (e-Pal) | 5000 |
| kR-H6-9 | 18 | Ac-DAFYTLVREIRQYRK (e-Pal) | 500 |
| kR-H6-10 | 19 | Pal-e-KAFYTLVREIRQY | 300 |
| kR-H6-12 | 20 | Pal-e-KFYTLVREIRQYR | 180 |
| kR-H6-11 | 21 | Ac-YQRIQRVLTYFK-e-Pal (all D) | 10 |
| kR-H6-13 | 22 | Ac-YQRKQRVLTYFK-e-Pal (all D) | 60 |
| kR-H6-14 | 23 | Pal-YQRKQRVLTYF (all D) | 40 |
| kR-H6-16 | 24 | Ac-VEDAFYTLVREIRQYR | >5000 |
| kR-H6-17 | 25 | Ac-AFYTLVREIRQYR | >5000 |
| kR-H6-18 | 26 | Pal-e-KAFYTLVREIRKHK | >1000 |
| kR-H6-19 | 27 | Pal-RYQRIQRVLTYFA (all D) | >1000 |
| kR-H6-20 | 28 | Pal-RYQRIQRVLTYF (all D) | 250 |
| kR-H6-21 | 29 | Pal-YQRIQRVLTYFA (all D) | 30 |
| kR-H6-22 | 30 | Pal-RYQRVQRVLTYFA (all D) | In testing |
| kR-H6-23 | 31 | Ac-RYQRIERVLTYFAK-e-Pal (all D) | 25 ± 10 |
| kR-H6-27 | 32 | Pal-e-KAFYTLVREIRQYRL | 280 ± 30 |
| kR-H6-28 | 33 | Pal-e-KAFYTLVRQIRQYRL | 250 ± 50 |
| kR-H6-30 | 34 | Ac-RYQRIQRVLTYFAK-e-Pal (all D) | 10 ± 5 |
| kR-H6-31 | 35 | Ac-LRYQRIQRVLTYFAK-e-Pal (all D) | 25 ± 10 |
| kR-H6-32 | 36 | Ac-RYQRIQRVLTYFK-e-Pal (all D) | 10 ± 4 |
| kR-H6-33 | 37 | Ac-YQRIQRVLTYFAK-e-Pal (all D) | 4.5 ± 1 |
| kR-H6-34 | 38 | Pal-YQRIQRVLTYF (all D) | 18 ± 5 |
| kR-H6-35 | 39 | Pal-Aib-YQRIQRVLTYF (all D) | 450 ± 50 |

TABLE 1-continued

Structure-activity relationships in derivatives of the C-terminal α-helix of K-Ras.

| Compound | SEQ ID NO | Structure | $GI_{50}$, nM |
|---|---|---|---|
| kR-H6-36 | 40 | Pal-YQRVQRVLTYF (all D) | 10 ± 5 |
| kR-H6-38 | 41 | Lau-YQRVQRVLTYF (all D) | 15 |
| kR-H6-39 | 42 | Lau-YQRVQRVLTYW (all D) | 90 ± 15 |
| kR-H6-40 | 43 | Myr-YQRVQRVLTYW (all D) | 20 ± 10 |
| kR-H6-41 | 44 | Cap-YQRVQRVLTYW (all D) | 180 ± 40 |
| kR-H6-42 | 45 | Lau-YKRVQRVLTYF (all D) | 300 ± 50 |
| kR-H6-43 | 46 | Lau-HQRVQRVLTYF (all D) | 300 ± 50 |
| kR-H6-44 | 75 | Lau-WQRVQRVLTYF (all D) | 1 ± 1 |
| kR-H6-45 | 76 | Lau-YQRVQRVLTYFC (all D) | In testing |
| kR-H6-46 | 77 | Ac-YQRVQRVLTYFC (all D) | In testing |
| kR-H6-47 | 78 | Lau-YQRVQRVLTYFA (all D) | 1 ± 1 |
| kR-H6-48 | 79 | Cap-YQRVQRVLTYFA (all D) | 0.8 ± 0.5 |
| kR-H6-49 | 80 | Cap-YQRVQRVLTYF (all D) | 0.8 |
| kR-H6-50 | 81 | Oct-YQRVQRVLTYF (all D) | 4 ± 1 |
| kR-H6-51 | 82 | Lau-YQRVQRVLTYFC (Fluo) (all D) | In testing |
| kR-H6-52 | 83 | Oct-YQRVQRVLTYFA (all D) | In testing |
| kR-H6-53 | 84 | Oct-WQRVQRVLTYFA (all D) | In testing |

Ac = acetylatation
Aib = amino-isobutiric acid
Doa = 2-dodecyl-alanine
Pal = palmitic acid
Lau = lauric or dodecanoic acid
Cap = caprylic or decanoic acid
Oct = octanoic acid The growth inhibitory activity of compounds was compared using the A549 human lung cancer cell line harboring constitutively active G12D Ras mutant with the help of an MTT assay. Peptide kR-H6-12 was the most effective in inhibiting cell growth with $GI_{50}$=180 nM (see Table 1). Stepwise extensions and truncations confirmed that the peptide had the optimal length (see Table 1).

Longer peptides (e.g., kR-H6-6) had lower potency. Further extensions led to further reduction in activity, possibly due to incorporation of negatively charged residues that interfere with cell entry (e.g., kR-H6-4). Compounds with palmitate on the N-terminal end were significantly more active than compounds with palmitic acid on the C-terminus (kR-H6-6 compared to kR-H6-8). Retro-inverso versions of the peptide turned out to be significantly more potent. For example, the retroinverso version of kR-H6-6 (kR-H6-23) was 10-fold more toxic to cancer cells (see Table 1).

Analysis of Ras structures suggested that Glu162 is not involved in formation of any salt bridges. Since negative charges interfere with cell entry, Glu162 was replaced with uncharged Gln, which resulted in additional 1.7-fold reduction in $GI_{50}$ (kR-H6-30). Incorporation of aminoisobutiric acid (Aib) is known to stabilize the helical fold of peptides and, therefore, was incorporated on the termini of the helix 6 derivatives to improve efficacy of inhibitors by facilitating more efficient folding and thus better mimicking the parent structure.

Example 2

This example demonstrates the characterization of the interaction of analogs of the C-terminal α-helix with Ras protein.

To study the interactions of the catalytic domain of K-Ras with kR-H6-6, $^{15}$N-labeled truncated K-Ras (1-166) lacking the hypervariable region was prepared as described in (Abraham et al., *Protein Expression and Purification*, 73(2): 125-131 (2010)). The purified protein was concentrated to 200 μM and titrated with a solution of kR-H6-6. The titration was followed by NMR $^{15}$N-edited HSQC spectra acquired on a 600 MHz Bruker spectrometer at 25° C.

Analysis of NMR titration data revealed a localized interaction of the peptide with the Switch I region of K-Ras with the most significant chemical shift perturbations found in residues Q25, N26, S32, T35, and E37. Intermolecular interactions between helix 6 of GTP-γ-S loaded K-Ras and the Switch I region of the neighboring K-Ras molecule previously were observed by x-ray crystallography. The Switch I region of Ras is critical for nucleotide binding and hydrolysis, and for interactions with effector proteins. Therefore, it is not surprising that kR-H6-6 binding to the Switch I region may interfere with K-Ras signaling.

Example 3

This example demonstrates the identification of analogs of the hypervariable region (HVR) of Ras.

The HVR of Ras protein has been suggested to be involved in targeting proteins to certain regions of cellular membranes and in interactions with effector proteins. HVR of Ras protein is naturally lipidated on the C-terminal ends. To generate the mimetics of HVR, peptides palmytilated on the C-terminal ends through ε-amino group of Lys that replaced farnesylated Cys of Ras were synthesized. The sequences of the peptides are presented in Table 2.

Since there was no structural data for any HVR of Ras, extensive structure-activity studies along with comparison of equivalent sequences in all isoforms of human Ras had to be undertaken (see FIG. 1 and Table 2). K-Ras-4A and N-Ras were palmitoylated on Cys 180 and 181, respectively, and were farnesylated on Cys 186, while H-Ras was palmitoylated on Cys 181 and 184 and farnesylated on Cys 186. For mimicking the palmitoylated Cys 180, 181, and 184 without significant decrease in peptide solubility, structurally similar, but less hydrophopic, norleucine residues ($L_N$) were introduced in the sequence of peptides.

The growth inhibitory activity of compounds was compared using the A549 human lung cancer cell line harboring constitutively active G12D Ras mutant with the help of an MTT assay. Optimization of compounds resulted in peptides that were significantly less potent than derivatives of helix 6; however, the compounds showed promising activity in vivo.

TABLE 2

Structure-activity relationships in derivatives of the hypervariable regions of Ras.

| Compound | SEQ ID NO | Structure | $GI_{50}$, μM |
|---|---|---|---|
| kR-4A-1 | 47 | Ac-RLKKISKEEKTPGSVKIKKK-e-Pal | 3.1 |
| kR-4A-2 | 48 | Ac-YRLKKISKEEKTPGK-e-Pal | 1.65 |
| kR-4A-4 | 49 | Ac-KTPGL$_N$VKIKKK-e-Pal | 0.7 |
| kR-4A-3 | 50 | Ac-YRLKKISKEEKTPGL$_N$VKIKKK-e-Pal | 1.9 |
| kR-4A-5 | 51 | Ac-KTPGAVKIKKK-e-Pal | 5 |
| kR-4A-6 | 52 | Ac-TPGL$_N$VKIKKK-e-Pal | >10 |
| kR-4A-7 | 53 | Ac-PGL$_N$VKIKKK-e-Pal | >10 |
| kR-4A-8 | 54 | Ac-GL$_N$VKIKKK-e-Pal | >10 |
| kR-4B-1 | 55 | Ac-KEKL$_N$SKDGKKKKKKSKTKK-e-Pal | 1.45 |
| kR-4B-2 | 56 | Ac-KL$_N$SKDGKKKKKKSKTKK-e-Pal | 1.4 |
| kR-4B-3 | 57 | Ac-KKKKKKSKTKK-e-Pal | 1.75 |
| kR-4B-4 | 58 | Ac-KKKKKSKTKK-e-Pal | 1.45 (0.5) |
| kR-4B-6 | 59 | Pal-KTKSKKKKK-NH$_2$ All-D | 1.7 |
| kR-4B-9 | 60 | e-Pal-KKTKSKKKKK-NH$_2$ All-D | 1.4 |
| kR-4B-7 | 61 | Ac-KKKKSKTKK-e-Pal | 2 |
| kR-4B-8 | 62 | Ac-KKKSKTKK-e-Pal | 2.3 |
| kR-4B-10 | 63 | Ac-KKSKTKK-e-Pal | In testing |
| HR-1 | 64 | Ac-ESGPGL$_N$L$_N$SL$_N$KK-e-Pal | 0.25 |
| HR-2 | 85 | Pal-KL$_N$L$_N$SL$_N$GPGSE-NH2 | In testing |
| HR-3 | 86 | Lau-KL$_N$L$_N$SL$_N$GPGSE-NH$_2$ | In testing |
| NR-1 | 65 | Ac-DGTQGL$_N$L$_N$GLPK-e-Pal | >10 |

Example 4

This example demonstrates the membrane binding activity of analogs of the HVR of Ras.

Membrane binding is thought to be important for Ras transforming activity. To assess the ability of K-Ras inhibitors to accumulate on the membrane, stabilized phospholipid bilayer nanodiscs were used as plasma membrane mimics.

Dipalmitoylphosphatidylcholine (DPPC) bilayers containing 5% dipalmitoyldiphosphatidylethanolamine (DPPE) stabilized by MSP1 scaffold protein were prepared. The DPPC lipids were chosen because they are among the most common components of the plasma membrane. The purified MSP1 protein was a generous gift from Dr. Sligar's lab, University of Illinois at Urbana, which also provided the procedure for preparation of nanodiscs. The preparation procedure involved mixing DPPC lipids with MSP1 at a 90:1 molar ratio in the presence of 100 mM cholate. Cholate was removed by slow dialysis. The assembled nanodiscs were purified by size-exclusion chromatography on a calibrated Superdex 200 column and immobilized on a surface plasmon resonance (SPR) sensor chip.

The presence of a primary amine group in DPPE provided a convenient site for cross-linking of nanodiscs to an SPR sensor chip. The noncross-linked dextran in the sample and reference cells was blocked by the coupling reagent. Four different peptides were used to study membrane binding by SPR. The HVR peptide represents the hypervariable region of K-Ras-4B and contains residues 165 through 183. The HVR peptide lacks post-translational modifications present in K-Ras4B. The second peptide is the HVR peptide conjugated to S-farnesyl L-cysteine methyl ester via a bifunctional cross-linker Sulfosuccinimidyl-4-(N-maleimidomethyl)cyclohexane-1-carboxylate (Sulfo-SMCC) (Pierce). The other two peptides were kR-4A-C1 and kR-4B-C1.

In all cases, with the exception of the HVR peptide, cooperative interaction with the phospholipid bilayers was observed. In this situation determination of true dissociation constants was not feasible. Instead, the data were analyzed using the Hill equation. The Hill coefficient describes the degree of binding cooperativity. While cooperativity for the HVR peptide was low with the Hill coefficient of 1.106±0.001, lipid modification significantly increased membrane binding cooperativity with the highest Hill coefficient of 6.15±0.02 observed for kR-4B-C1. The Hill coefficient for the HVR peptide modified with S-farnesyl L-cysteine methyl ester was 5.725±0.002. Among lipidated peptides kR-4A-C1 exhibited the lowest membrane binding cooperativity with the Hill coefficient of 3.606±0.003.

Cooperative interaction of the peptides with the membrane phospholipids not only enhances their binding affinity but also facilitates their clustering on the plasma membrane for a more potent effect on K-Ras. Among the peptides studied for their binding to the phospholipid bilayers, the palmitoylated kR-4B-1 peptide showed the best cooperative interactions with membrane lipids. The ability of kR-4B-1 to cluster on the phospholipid bilayers was superior even to the HVR with native farnesyl and methyl ester modifications.

Example 5

This example demonstrates the biological activity of Ras inhibitors.

Figure 2:
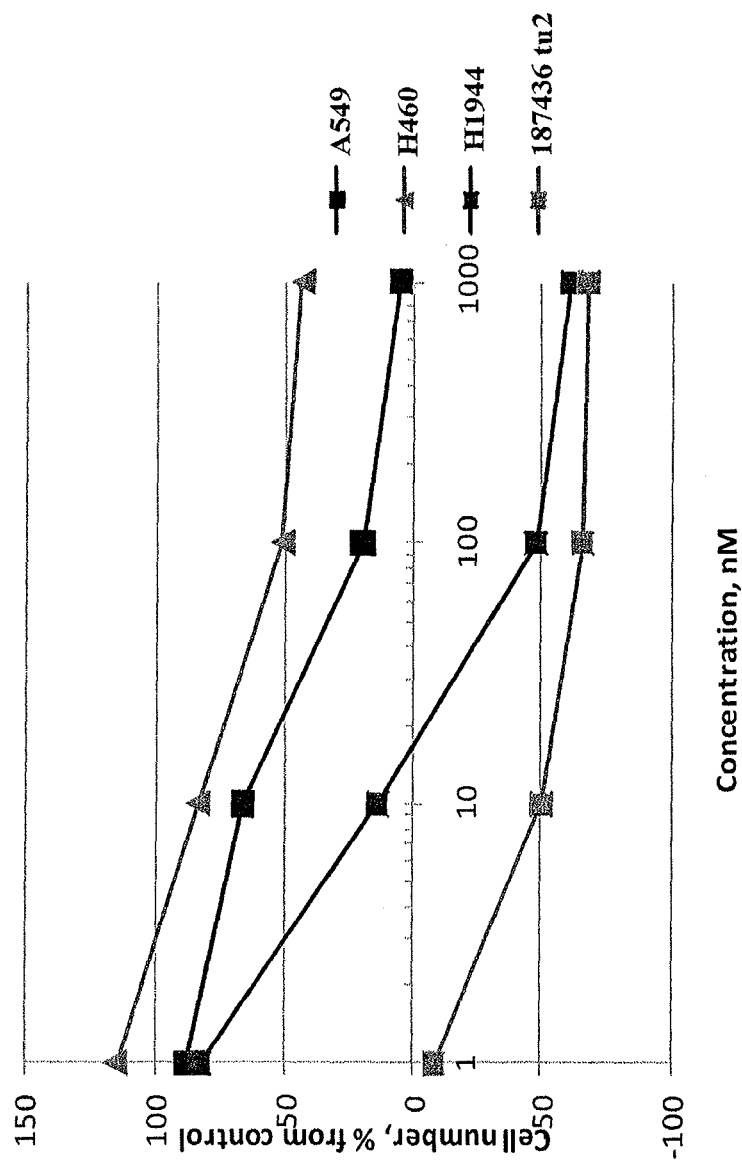
FIG. 2 is a graph illustrating growth inhibition in human lung tumor cell lines (A549, H460, and H1944) and a mouse astrocytoma cell line (187436 tu2) expressing mutated K-Ras by treatment with a Ras inhibitor (KR-H6-23). The concentration (nM) of inhibitor is represented on the x-axis and the cell number (percent of control) is represented on the y-axis.
Figure 3:
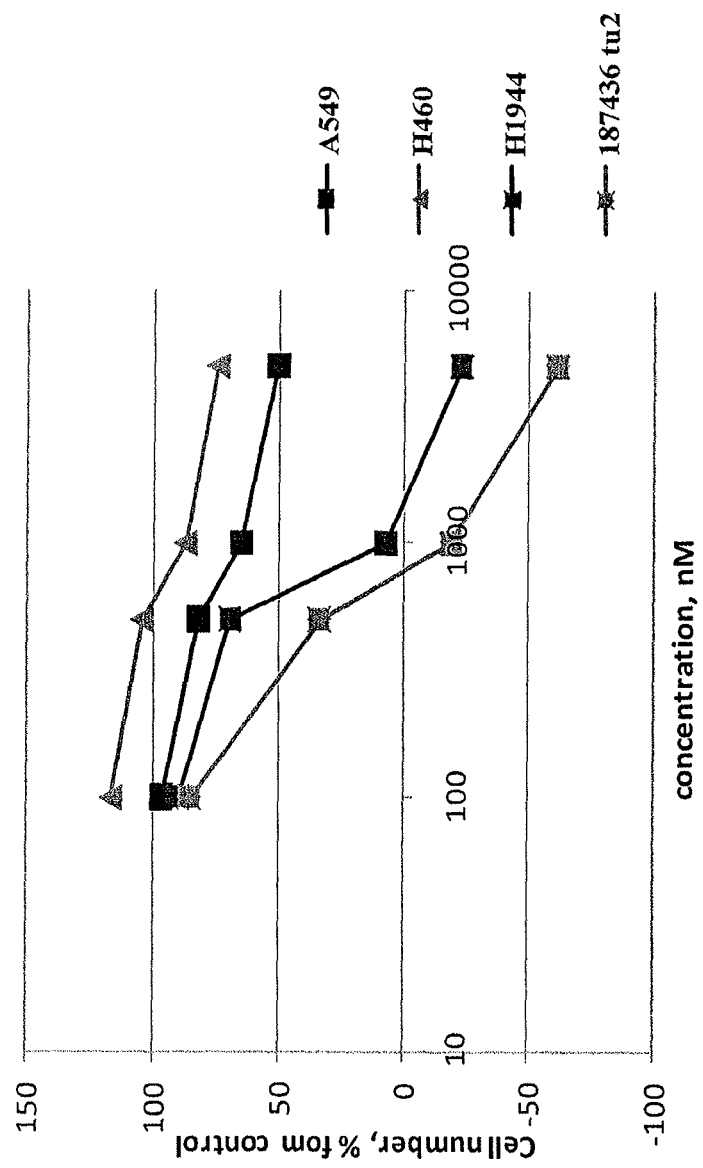
FIG. 3 is a graph illustrating growth inhibition in human lung tumor cell lines (A549, H460, and H1944) and a mouse astrocytoma cell line (187436 tu2) expressing mutated K-Ras by treatment with a Ras inhibitor (KR-4A-4). The concentration (nM) of inhibitor is represented on the x-axis and the cell number (percent of control) is represented on the y-axis.

Activity of compounds towards different cell lines varied significantly even if the cells expressed identical versions of mutated Ras. Relative activities for different cells were similar for compounds mimicking helix 6 and HVR of K-Ras (see FIGS. 2 and 3), suggesting that they may act by similar mechanisms in spite of targeting different regions of Ras protein. Interestingly, mouse cell line 187436 tu2 with well-defined genetic alterations was the most sensitive to the compounds (see FIGS. 2 and 3). The cell line was generated from astrocytoma developed in a transgenic mouse harboring a G12D mutation in K-Ras and inactivation of the Rb gene.

Human lung cancer cell lines, A549, H460, and H1944, are known to have additional oncogenic mutations. Consequently, these cell lines are likely to have populations of cells resistant to Ras inhibitors and, thus, will appear less sensitive to the compounds. Human lung cancer cell lines with identical Ras mutations also have been reported to have different degree of "Ras addiction" or sensitivity to Ras inhibition.

Figure 4:
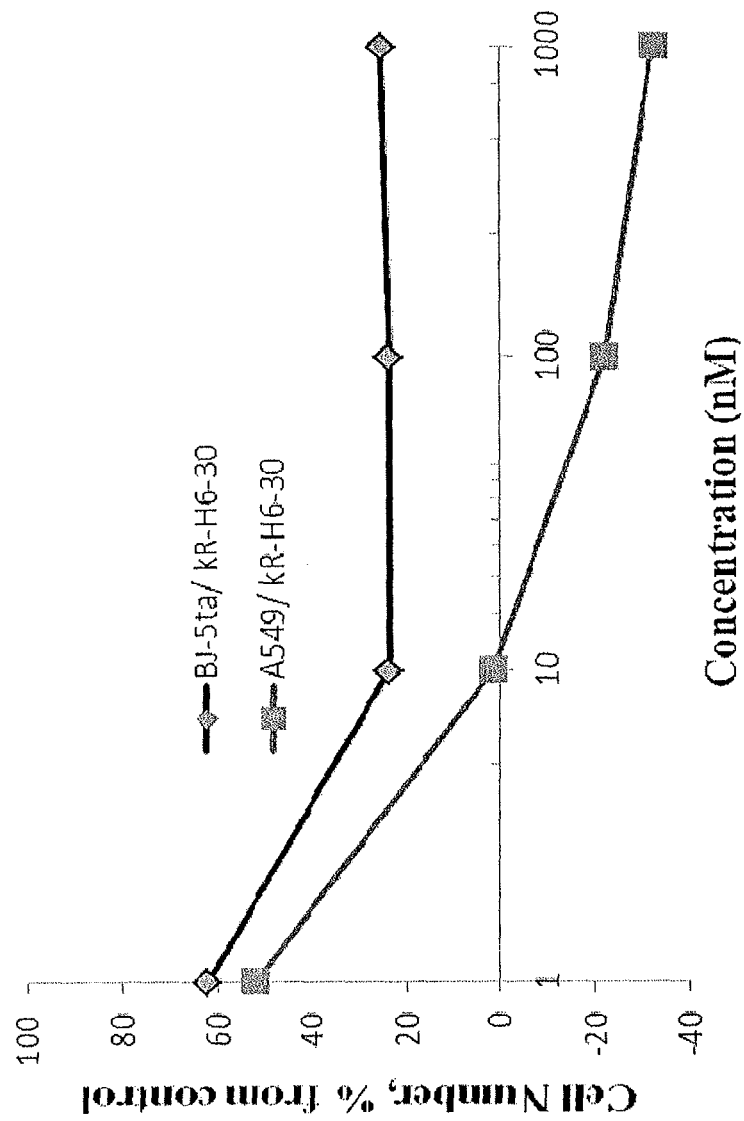
FIG. 4 is a graph illustrating growth inhibition in a breast epithelial cell line (BJ-5ta, immortalized by transfection of normal cells with human Telomerase Reverse Transcriptase (hTERT)-expressing plasmid) and a human lung tumor cell line (A549) by treatment with a Ras inhibitor (kR-H6-30). The concentration (nM) of inhibitor is represented on the x-axis and the cell number (percent of control) is represented on the y-axis.

The inventive Ras inhibitors were much more toxic even to less sensitive lung cancer cells than to regular immortalized fibroblasts (see FIG. 4). No killing of epithelial cells was observed even for micromolar concentrations of the inhibitors suggesting that a therapeutic window should exist that will allow selective elimination of tumor cells with the help of the inventive helix 6 analogs.

Analogs of HVR were on average twice as potent in growth inhibition of cells with mutated K-Ras as the cells with wild-type protein (see Table 3).

TABLE 3

Growth inhibitor activity of HVR analogs evaluated on thoracic malignancy cell lines.

| Tumor type | Cell line | K-Ras status | kR-4A-3 $GI_{50}$ (µM) | kR-4B-3 $GI_{50}$ (µM) |
|---|---|---|---|---|
| lung adenocarcinoma | A549 | Mutant | 3.1 | 1.45 |
| lung adenocarcinoma | H2009 | Mutant | 2.2 | 2.9 |
| lung adenocarcinoma | H23 | Mutant | 2.6 | 2.4 |
| lung adenocarcinoma | Calu 6 | Mutant | 3.0 | 2.7 |
| broncheoalveolar | H358 | Mutant | 2.2 | 2.0 |
| lung squamous cell carcinoma | H157 | Mutant | 2.4 | 1.5 |
| large cell carcinoma | H460 | Mutant | 1.5 | 1.0 |
| lung adenocarcinoma | Calu3 | WT | 5.9 | 2.2 |
| lung adenocarcinoma | H2882 | WT | 4.0 | 3.0 |
| lung squamous cell carcinoma | HCC95 | WT | 5.1 | 3.3 |
| lung squamous cell carcinoma | HCC15 | WT | 7.4 | 3.1 |
| MPM | H2373 | WT | 6.1 | 4.8 |
| MPM | H2461 | WT | >10.0 | >10.0 |
| MPM | H2596 | WT | 8.2 | 6.2 |
| MPM | HP-1 | WT | >10 | 7.3 |

MPM = malignant pleural mesothelioma
WT = wild-type

Although not wishing to be bound by any theory, the inventors hypothesize that the differences in sensitivity are relatively small because Ras gets activated in tumor cells by multiple mechanisms including activation of receptor tyrosine kinases. Since Ras functions downstream of important regulators of tumor cell growth, such as epithelial growth factor receptor, insulin-like growth factor 1 receptor, and MET, its activation is a common event in tumors. Thus, widespread sensitivity of tumor cell lines to Ras inhibitors is not surprising.

Figure 5:
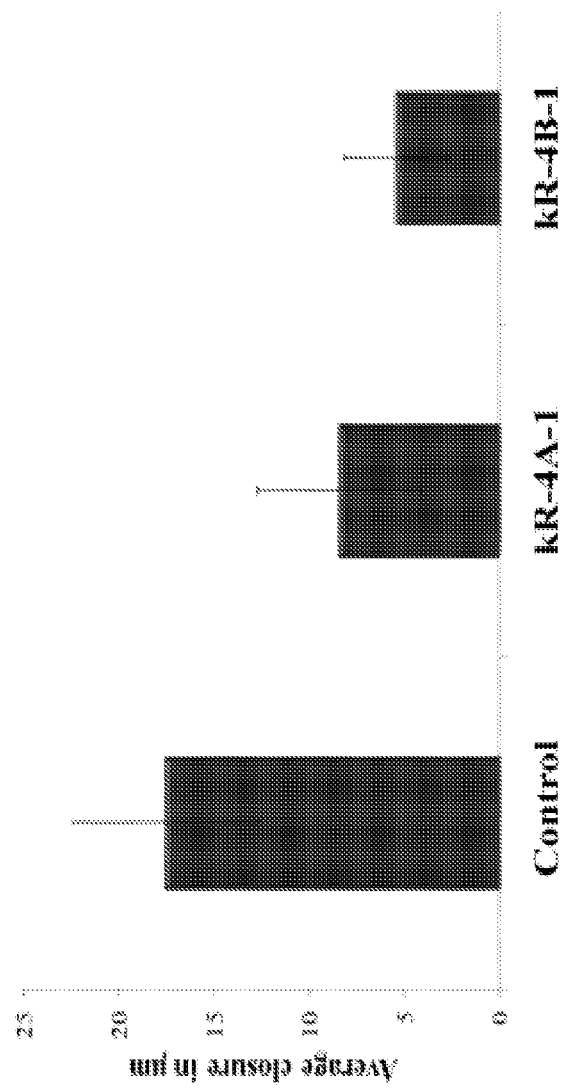
FIG. 5 is a graph illustrating the inhibition of HCC15 cell motility by treatment with Ras inhibitors (kR-4A-1 and kR-4B-1). The average closure in μm is indicated on the y-axis for control.
Figure 6:
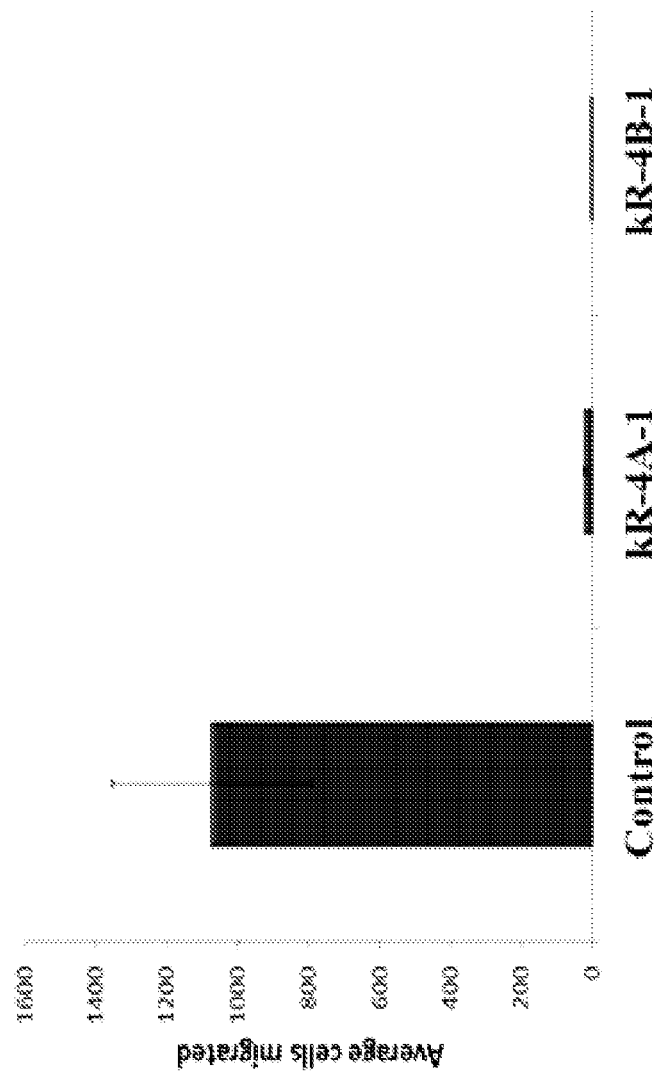
FIG. 6 is a graph illustrating the inhibition of NCC15 cell migration by treatment with Ras inhibitors (kR-4A-1 and kR-4B-1). The average number of cells migrated is indicated on the y-axis.
Figure 7:
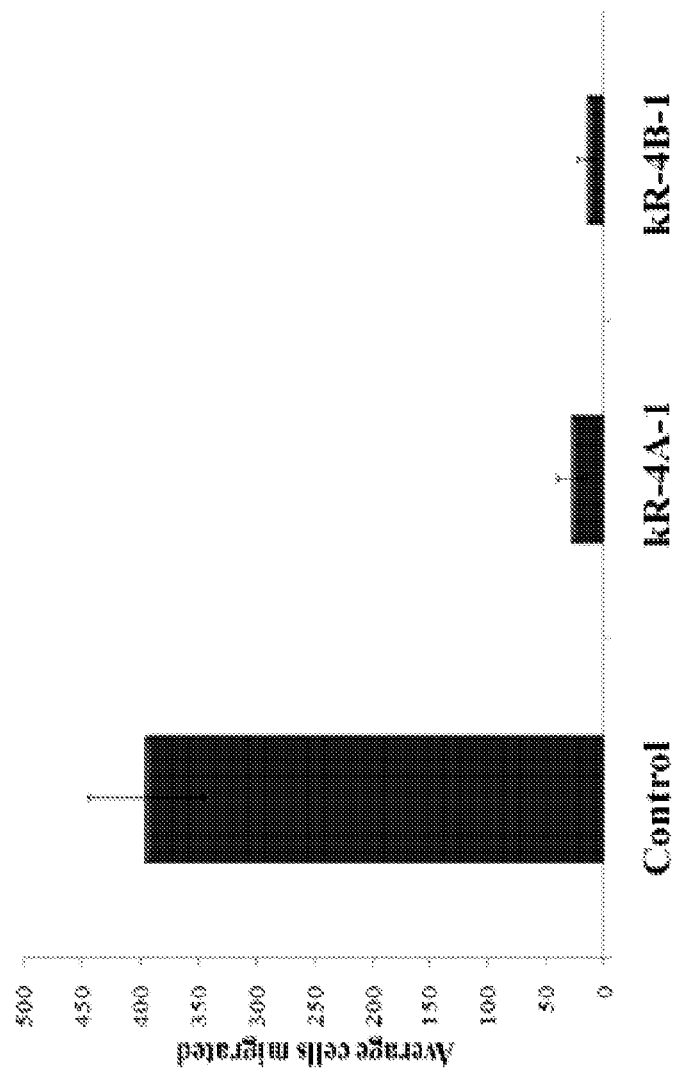
FIG. 7 is a graph illustrating the inhibition of HCC15 cell invasion by treatment with Ras inhibitors (kR-4A-1 and kR-4B-1). The average number of cells migrated is indicated on the y-axis.

Using a "wound closure" assay on HCC15 cells, wherein the closure of a "wound" or gap in a cell monolayer is monitored and measured, demonstrated remarkable reduction in cell motility in the presence of analogs of HVR and helix 6 (see FIG. 5). The rate of migration and invasion was determined using Boyden Chambers (Millipore) in accordance with the manufacturer's protocol. The migration and invasion rate was dramatically reduced in the presence of $IC_{25}$ concentration of the analogs (see FIGS. 6 and 7). The data suggests that Ras inhibitors have an effect on tumor growth and its metastatic ability.

A further experiment was undertaken to determine the effect of analogs of helix 6 and HVR on the amount of K-Ras protein in cancer cells. H2009 (lung adenocarcinoma cells) and H2592 (plural mesothelioma cells) were exposed to varying concentrations (0-3.0 μM) of kR-4A-3, kR-4B-3, or kR-H6-3 for 18 hours. The cells then were lysed and the lysate was analyzed by Western blot using anti-Ras mAb (Cell Biolabs, Inc.). Inhibitors of Ras reduced the amount of Ras protein in lung cancer cells in a concentration-dependent manner.

H2592 cells were exposed to $GI_{50}$ concentrations of kR-4A-3 or kR-H6-3 for 18 hours, fixed with 4-7% (w/v) paraformaldehyde for 30 minutes, permeabilized with 0.1% (v/v) Triton X-100, and immunostained with anti-Ras mAb (Cell Biolabs, Inc.). Goat anti-mouse antibodies with Alexa Fluor TM 594 (red) were used to visualize the anti-Ras mouse mAb. Immunohistochemistry of treated cells showed not only reduction in protein levels compared to control cells treated with vehicle (0.1% DMSO), but also a lack of characteristic punctuate pattern of K-Ras distribution.

Example 6

This example demonstrates the effect of Ras inhibitors on tumor growth in mice.

$2\times10^6$ H358 human lung cancer cells with mutated K-Ras were implanted subcutaneously (s.c.) in nude mice. When tumors reached measurable size, 10 mg/kg kR-4A-8 or control (DMSO in buffer) was injected s.c. near the tumor every second day for 20 days. No toxicity was detected during treatment or necropsy.

Figure 8:
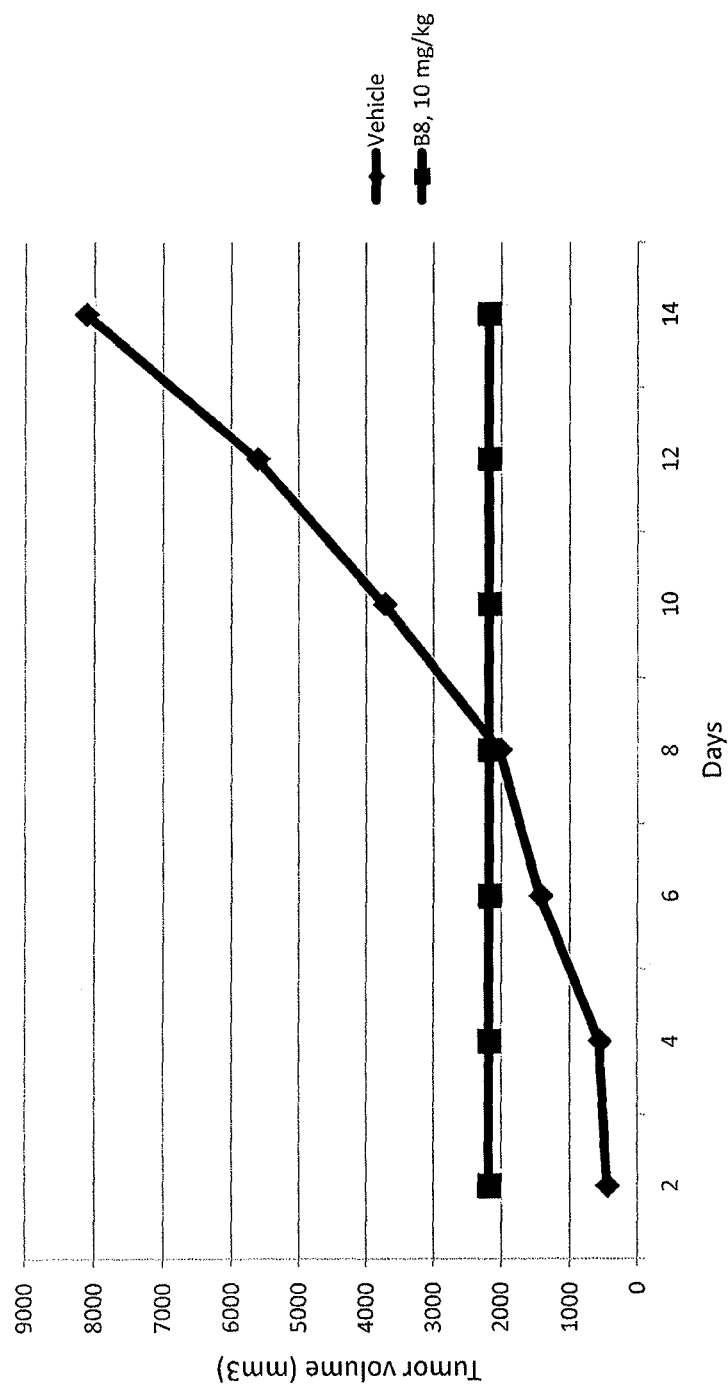
FIG. 8 is a graph illustrating the suppression of growth of an H358 human tumor in nude mice. Tumor volume change (mm$^3$) for control (DMSO vehicle) (◇) or 10 mg/kg kR-4B-8 treated (B8) (□) mice is indicated on the y-axis. The number of days is indicated on the x-axis.

Administration of kR-4B-8 abolished the growth of a very aggressive tumor formed by broncheoalveolar carcinoma H358 cells (see FIG. 8). Furthermore, tumors at the time of sacrifice were much smaller in treated (e.g., 0.35 g) versus control (e.g., 1.21 g) mice.

Example 7

This example further demonstrates the effect of Ras inhibitors on tumor growth in mice.

Lewis lung carcinoma LL/2 (LLC1) (ATCC Catalog No. CRL-1642) cells were grown in DMEM medium containing 10% FBS. Cells were trypsinized and suspended in PBS. $3\times10^6$ LLC1 cells in 200 μl PBS were injected subcutaneously to the right flank of 8 weeks old female CB57Bl/6 mice.

Ras inhibitor injections started 2 weeks after LLC1 injections when tumors were at least 3 mm in diameter. For injections, solid kR-H6-48 was initially dissolved in DMSO to yield 20 mg/mL stock solution. DMSO stocks were diluted 20-fold in PBS pre-warmed to 35-37° C. 200 μl of the resulting solution (10 mg/kg dose) was injected subcutaneously near the tumor(s) every second day. The control group received 200 μl of 5% DMSO in PBS. Tumor size was measured with a caliper before each injection. The mice were sacrificed when the tumors reached maximal allowed size.

Figure 9:
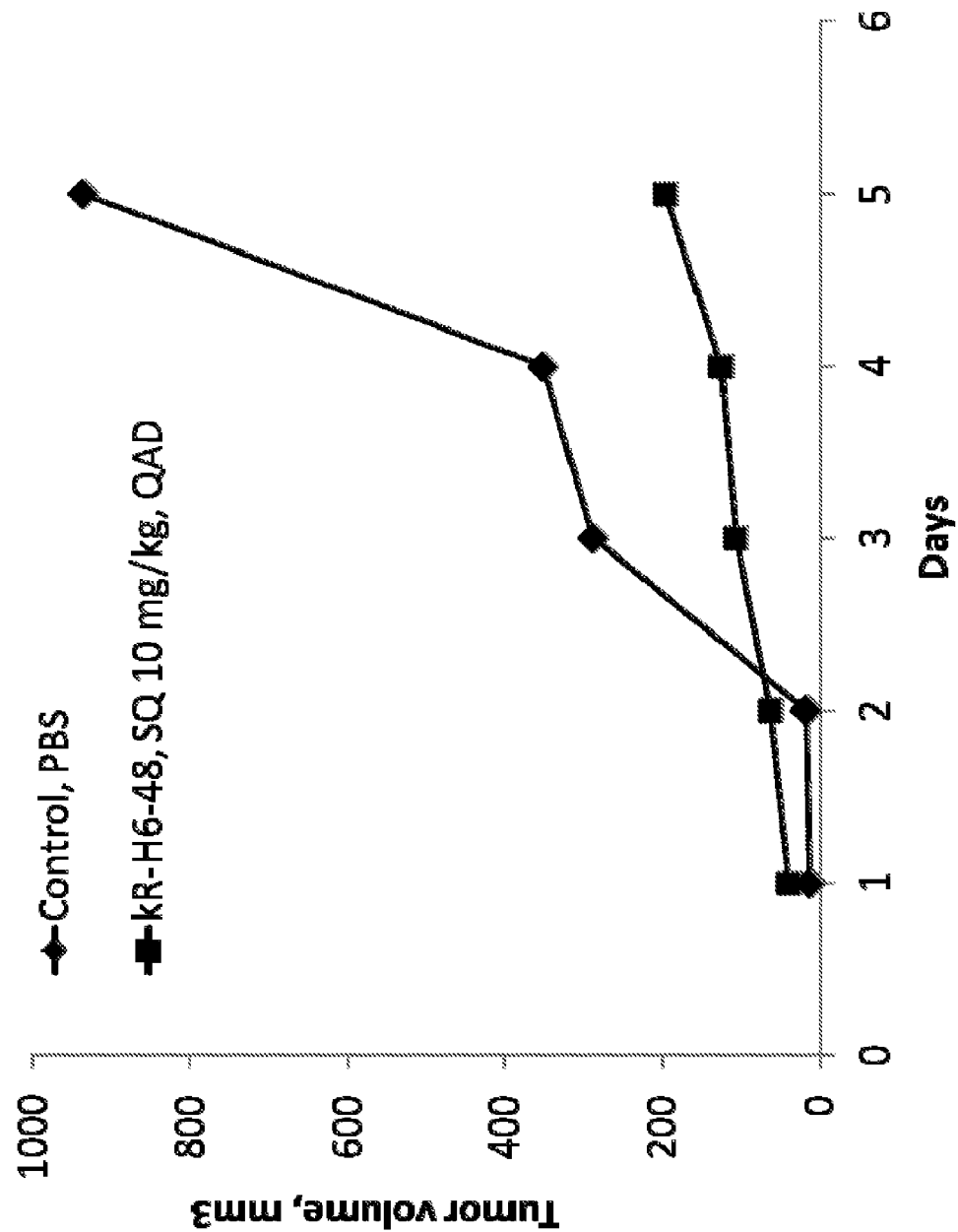
FIG. 9 is a graph illustrating the effect of a Ras inhibitor (kR-H6-48) on Lewis Lung Carcinoma isograft growth in female mice. Tumor volume (mm$^3$) for control (PBS) (◇) or 10 mg/kg KR-H6-48 treated (□) mice is indicated on the y-axis. The number of days is indicated on the x-axis.

Administration of kR-H6-48 inhibited LLC1 isograft growth in female mice (see FIG. 9).

Example 8

This example demonstrates that Ras inhibitors reduce the amount of activated Ras in lung cancer cells.

H358 human lung cancer cells were grown in 6-well plates in DMEM medium containing 10% FBS. When the cells were about 70% confluent, the medium was replaced with DMEM containing 1% FBS. Two hours later, Ras inhibitors (kR-H6-48, HR-1, kR-4A-4, or kR-4B-2) were added to provide a final concentration of 5 μM.

After varying exposure times, the cells were rinsed with PBS and lysed. The lysates were cleared by centrifugation, incubated with immobilized Raf-RBD beads (which bind Ras) and analyzed by Western blot using manufacturer's protocols (Cytoskeleton, Inc., Denver, Colo.; Catalog No. BK008). The bands corresponding to active (GTP-bound) Ras were quantified with the help of MIPAV software.

Figure 10:
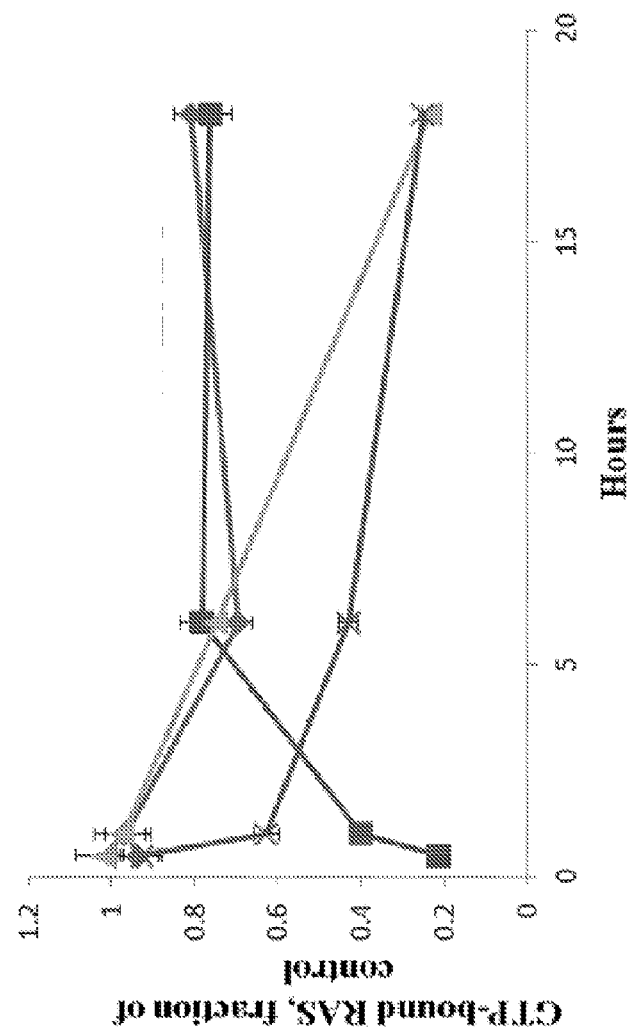
FIG. 10 is a graph illustrating the reduction in activated (GTP-bound) Ras in lung cancer cells by Ras inhibitors. GTP-bound Ras (fraction of control) for kR-H6-48 (◇), HR-1 (□), kR-4A-4 (Δ), and kR-48-2 (x) is indicated on the y-axis. The number of hours is indicated on the x-axis.

Administration of the inhibitors reduced the amount of activated (GTP-bound) Ras in lung cancer cells (see FIG. 10).

Example 9

This example demonstrates that Ras inhibitors reduce growth of Ras-dependent cancer cells.

Ras-dependent cancer cells (H358 human lung cancer cells, SKBR3 human breast cancer cells, SKOV3 human ovarian cancer cells, ID8 murine ovarian cancer cells, and MPR-178 murine prostate cancer cells) were grown in DMEM medium containing 1% FBS and exposed to varying concentrations of Ras inhibitors (kR-H6-48 and HR-1) for 48 hours. Cell growth was evaluated utilizing an MTT ((3-(4,5-Dimethylthiazol-2-yl)-2,5-diphenyltetrazolium) assay. The absorbance of the wells at 544 nm was determined by a FLUOstar/POLARstar Galaxy (BMG Lab Technologies GmbH, Ortenberg, Germany) microplate reader. The assays were performed on untreated (control) and test cells. Cellular responses were calculated from the data using the following formula: $100\times[(T-T_0)/(C-T_0)]$ for $T>T_0$ and $100\times[(T-T_0)/T0]$ for $T<T_0$, wherein $T_0$ corresponds to cell density at the time of drug addition.

Figure 11A:
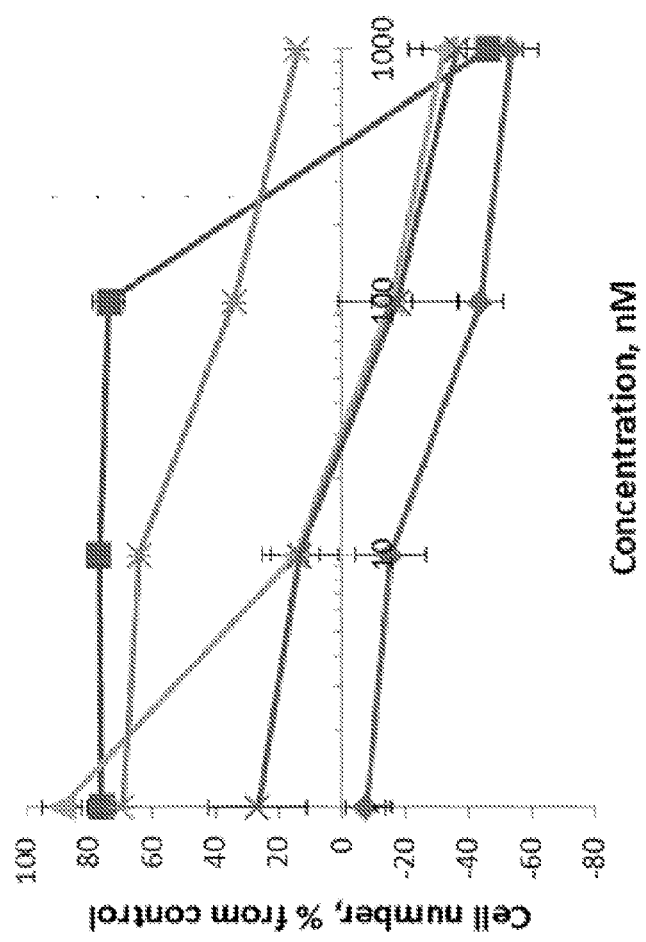
FIGS. 11A-B are graphs illustrating the growth inhibition of Ras-dependent cancer cells by kR-H6-48 (A) and HR-1 (B). The cell number (percent of control) of H358 (◇), SKBR3 (□), SKOV3 (Δ), MPR-178 (x), and ID8 (*) cells is indicted on the y-axis. The concentration (nM) is indicated on the x-axis.
Figure 11B:
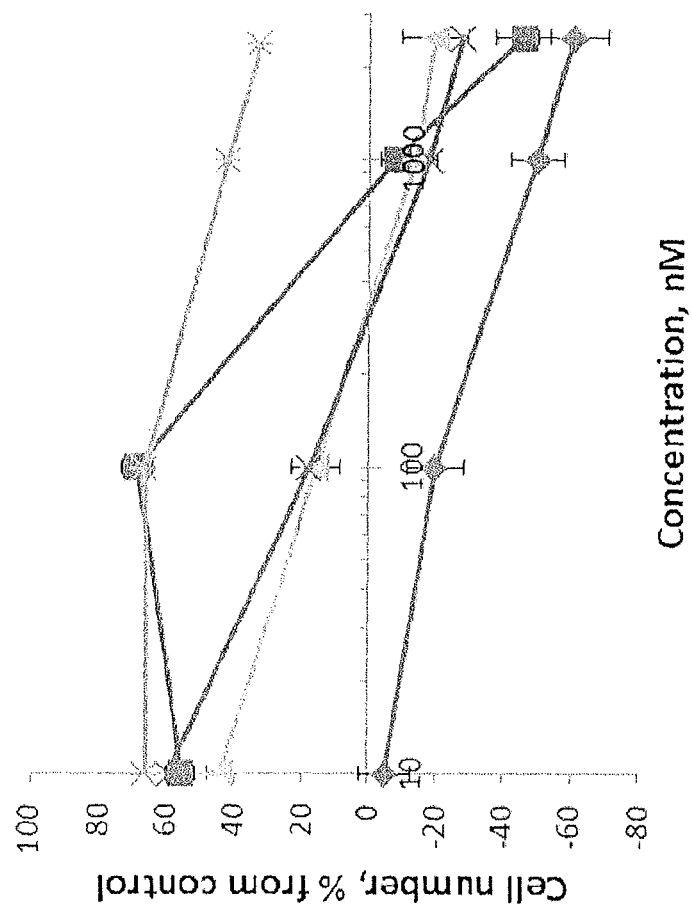
Figure 12:
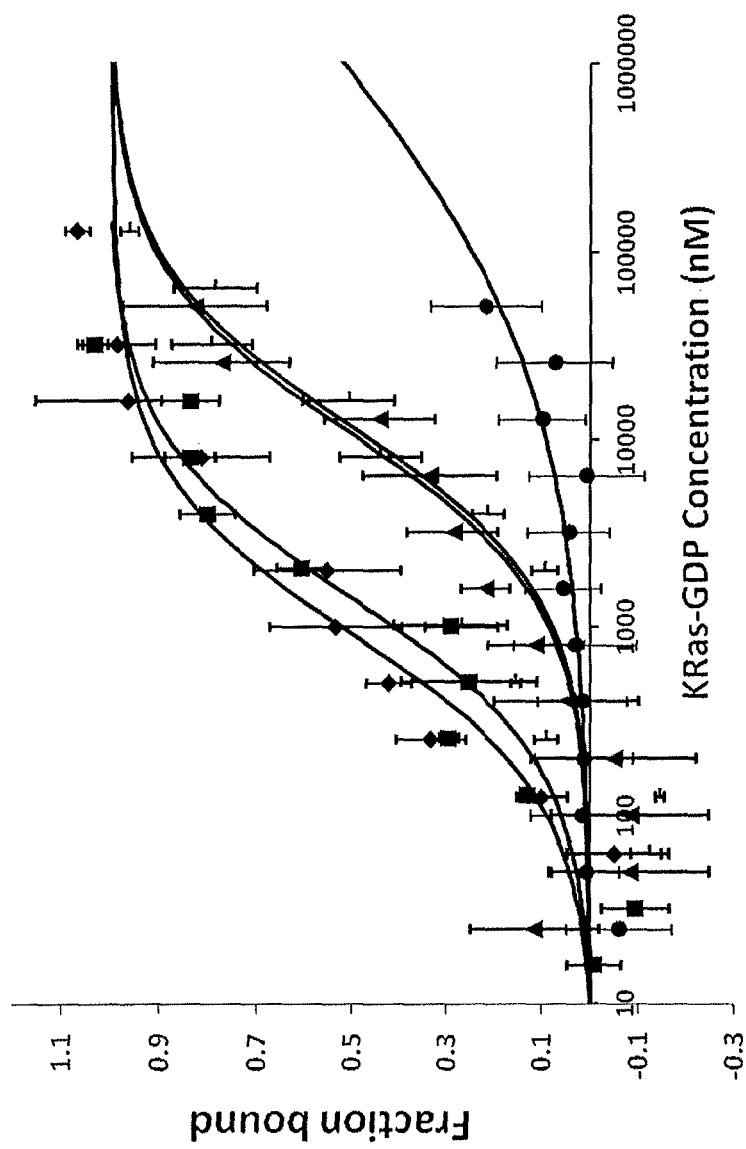
FIG. 12 illustrates the direct interaction of fluorescent lipopeptide analogs of Ras. The bound fraction of kR-H6-57 (□), kR-H6-58 (◇), kR-4B-14 (Δ), HR-6 (○), and kR-4A-11 (–) in dodecylphosphocholine (DPC) micelles is indicated on the y-axis. The K-Ras-GDP concentration (nM) is indicated on the x-axis. The $K_D$ for each inhibitor is as follows: 1.44±0.16 μM (kR-H6-57), 0.89±0.13 μM (kR-H6-58), 10.8±1.6 μM (kR-4B-14), >100 μM (HR-6), and 11.8±1.3 μM (kR-4A-11).
Figure 13A:
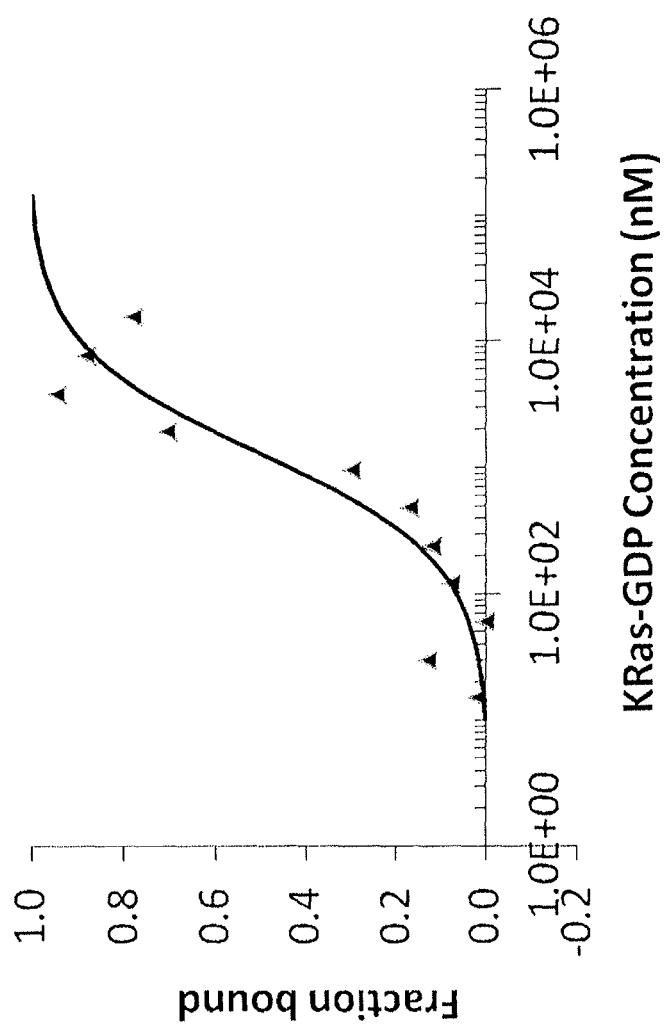
FIGS. 13A-D illustrate that the affinity of Ras inhibitors towards recombinant K-Ras depends on the membrane-mimicking environment and is higher in bicelles than in micelles. The bound fraction of kR-48-14 in DMPC/DHPC bicelles (A), kR-4B-14 in DPC micelles (B), kR-H6-57 in DMPC/DHPC bicelles (C), and kR-H6-57 in DPC micelles (D) is indicated on the y-axis. The K-Ras-GDP concentration (nM) is indicated on the x-axis. The $K_D$ for each inhibitor is as follows: 1.3±0.1 μM (kR-4B-14 in DMPC/DHPC bicelles), 10.8±1.6 μM (kR-4B-14 in DPC micelles), 86.3±7.6 μM (kR-H6-57 in DMPC/DHPC bicelles), and 1.4±1.6 μM (kR-H6-57 in DPC micelles).
Figure 13B:
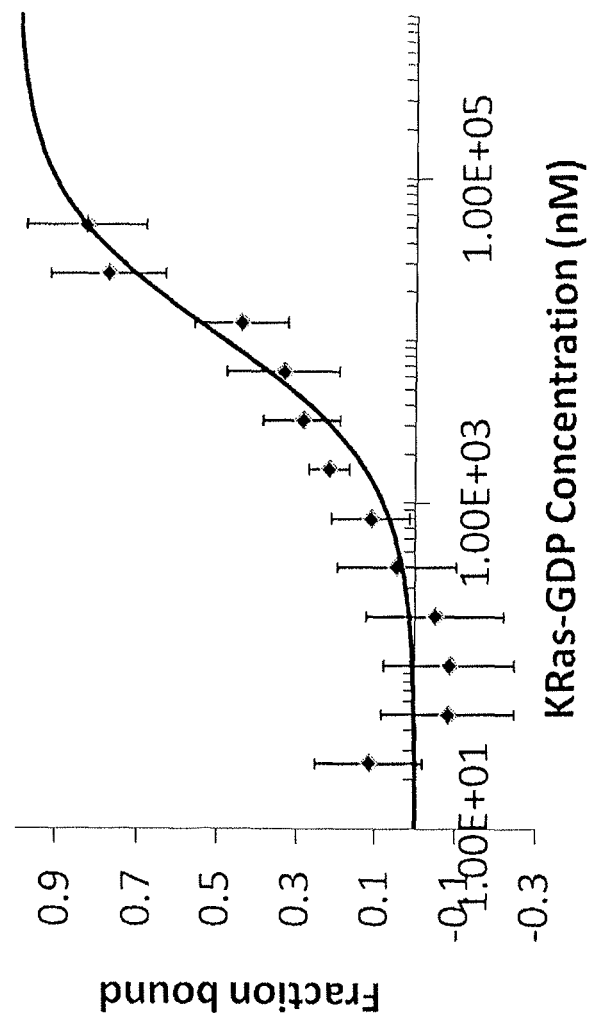
Figure 13C:
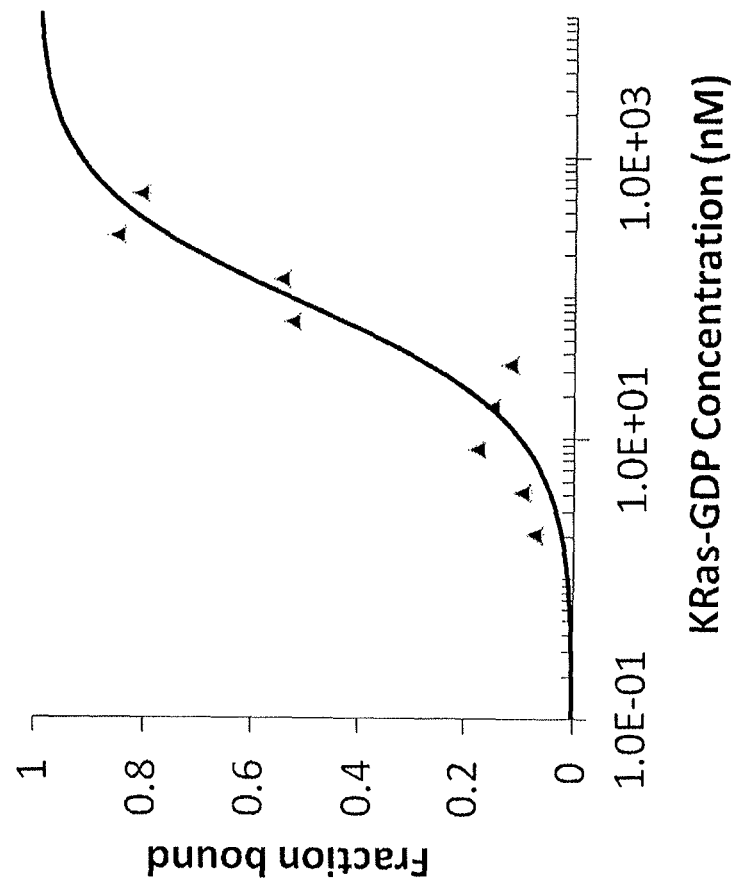
Figure 13D:
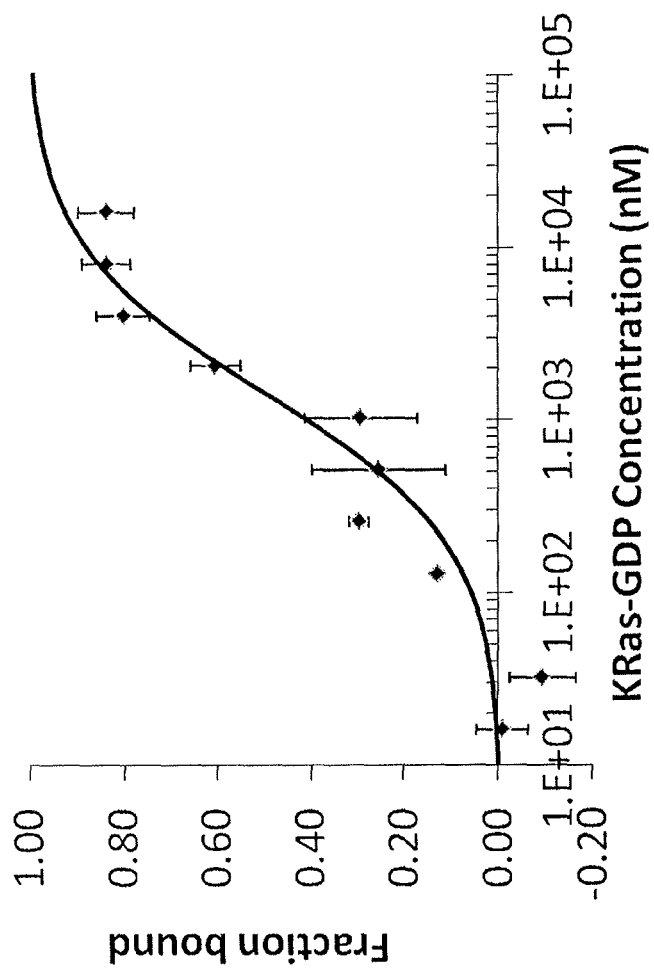

Administration of the inhibitors potently inhibited growth of Ras-dependent cancer cells (see FIGS. 11A-B).

Example 10

This experiment demonstrates high affinity binding of lipopeptide analogs of HVR and helix 6 to recombinant K-Ras.

Recombinant truncated K-Ras protein (1-166) was prepared as described in Abraham et al., *Protein Expr. Purif.*, 73(2): 125-31 (2010). Inhibitors labeled with fluorescein were dissolved in DMPC/DHPC bicelles (q=2.7, lipids=5% w/v) to an approximate concentration of 1 mg/mL. The exact concentration was determined by measuring UV absorbance in the range of 480-496 nm. Fluorescein extinction coefficient equal to 68,000 $M^{-1}cm^{-1}$ value was used to calculate the exact concentration of the inhibitor.

TABLE 4

Inhibitors used in microscale thermophoresis experiments.

| Compound | SEQ ID NO | Structure |
|---|---|---|
| kR-H6-57 | 87 | K(ε-Pal)C(Fluo)FYTLVREIRQYR |
| kR-H6-58 | 88 | Ac-C(Fluo)FYTLVREIRQYR |
| kR-4B-14 | 89 | Ac-C(Fluo)KKKKKSKTKK(ε-Pal) |
| kR-4A-11 | 90 | Ac-C(Fluo)KTPGL$_N$VKIKKK(ε-Pal) |
| HR-6 | 91 | Ac-C(Fluo)ESGPGL$_N$L$_N$SL$_N$KK(ε-Pal) |

Inhibitors were diluted to an appropriate concentration with bicelles solution. Titration series (16 binding mixtures) were prepared containing constant amounts of fluorescent peptide (5 nM for kR-H6-57 and 40 nM for other inhibitors) in each sample and varying concentrations of recombinant Ras protein. The buffer composition for the protein dilution contained 25 mM Tris-citrate pH 6.5, 150 mM NaCl, 10 mM $MgCl_2$, 5% Glycerol, 1 mM EDTA, and 1 mM β-mercaptoethanol. Measurements were taken in standard treated capillaries on a Monolith NT.115 instrument (NanoTemper Technologies GmbH, Germany) using 20% IR-laser power and LED excitation source with λ=470 nm at ambient temperature. NanoTemper Analysis 1.2.20 software was used to fit the data and determine the apparent KD values.

Microscale thermophoresis performed in the presence of membrane-mimicking micelles and/or bicelles confirmed direct interaction of fluorescent lipopeptide analogs of the HVR and helix 6 with recombinant truncated GDP-loaded K-Ras (see FIGS. 12 and 13A-D). The affinity of inhibitors towards recombinant K-Ras depended on the membrane-mimicking environment and was higher in bicelles than micelles (see FIG. 13A-D).

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

The invention claimed is:

1. A peptide or peptidomimetic comprising the amino acid sequence of any one of SEQ ID NOs: 10-46 or 75-84, or the inverse sequence thereof,
wherein the peptide or peptidomimetic comprises about 30 or fewer amino acids.

2. A peptide or peptidomimetic comprising the inverse sequence of the amino acid sequence of any one of SEQ ID NOs: 66, SEQ ID NO: 67, or SEQ ID NO: 68, wherein the peptide or peptidomimetic comprises about 30 or fewer amino acids.

3. The peptide or peptidomimetic of claim 1 comprising about 20 or fewer amino acids.

4. The peptide or peptidomimetic of claim 1 comprising one or more D-amino acids.

5. The peptide or peptidomimetic of claim 1 further comprising a cell-penetrating motif.

6. The peptide or peptidomimetic of claim 1 comprising a terminal fatty acid group.

7. The peptide or peptidomimetic of claim 6 comprising an N-terminal palmitoyl residue.

8. The peptide or peptidomimetic of claim 6 comprising an N-terminal myristoyl residue.

9. The peptide or peptidomimetic of claim 6 comprising an N-terminal lauryl residue.

10. The peptide or peptidomimetic of claim 6 comprising an N-terminal octanoyl residue.

11. A pharmaceutical composition comprising the peptide or peptidomimetic of claim 1 and a carrier.

12. A method for treating cancer in a host, wherein the cancer is breast cancer, lung cancer, ovarian cancer or prostate cancer, comprising administering to the host the peptide or peptidomimetic of claim 1, whereby the cancer is treated.

13. A peptide or peptidomimetic comprising the amino acid sequence of SEQ ID NO: 79, wherein the peptide or peptidomimetic comprises about 30 or fewer amino acids.

14. The peptide or peptidomimetic of claim 2 comprising about 20 or fewer amino acids.

15. The peptide or peptidomimetic of claim 2 comprising one or more D-amino acids.

16. The peptide or peptidomimetic of claim 2 further comprising a cell-penetrating motif.

17. The peptide or peptidomimetic of claim 2 comprising a terminal fatty acid group.

18. The peptide or peptidomimetic of claim 17 comprising an N-terminal palmitoyl residue.

19. The peptide or peptidomimetic of claim 17 comprising an N-terminal myristoyl residue.

20. The peptide or peptidomimetic of claim 17 comprising an N-terminal lauryl residue.

21. The peptide or peptidomimetic of claim 17 comprising an N-terminal octanoyl residue.

22. A pharmaceutical composition comprising the peptide or peptidomimetic of claim 2 and a carrier.

* * * * *

SEQUENCE LISTING

```
<160> NUMBER OF SEQ ID NOS: 91

<210> SEQ ID NO 1
<211> LENGTH: 189
<212> TYPE: PRT
<213> ORGANISM: Homo sapiens

<400> SEQUENCE: 1

Met Thr Glu Tyr Lys Leu Val Val Val Gly Ala Gly Gly Val Gly Lys
1               5                   10                  15

Ser Ala Leu Thr Ile Gln Leu Ile Gln Asn His Glu Val Asp Glu Tyr
            20                  25                  30

Asp Pro Thr Ile Glu Asp Ser Tyr Arg Lys Gln Val Val Ile Asp Gly
        35                  40                  45

Glu Thr Cys Leu Leu Asp Ile Leu Asp Thr Ala Gly Gln Glu Glu Tyr
    50                  55                  60

Ser Ala Met Arg Asp Gln Tyr Asn Arg Thr Gly Glu Gly Phe Leu Cys
65                  70                  75                  80

Val Phe Ala Ile Asn Asn Thr Lys Ser Phe Glu Asp Ile His His Tyr
                85                  90                  95

Arg Glu Gln Ile Lys Arg Val Lys Asp Ser Glu Asp Val Pro Met Val
            100                 105                 110

Leu Val Gly Asn Lys Cys Asp Leu Pro Ser Arg Thr Val Asp Thr Lys
        115                 120                 125

Gln Ala Gln Asp Leu Ala Arg Ser Tyr Gly Ile Pro Phe Ile Glu Thr
    130                 135                 140

Ser Ala Lys Thr Arg Gln Arg Val Glu Asp Ala Phe Tyr Thr Leu Val
```

```
                 145                 150                 155                 160

Arg Glu Ile Arg Gln Tyr Arg Leu Lys Lys Ile Ser Lys Glu Glu Lys
                 165                 170                 175

Thr Pro Gly Cys Val Lys Ile Lys Lys Cys Ile Ile Met
                 180                 185

<210> SEQ ID NO 2
<211> LENGTH: 188
<212> TYPE: PRT
<213> ORGANISM: Homo sapiens

<400> SEQUENCE: 2

Met Thr Glu Tyr Lys Leu Val Val Val Gly Ala Gly Gly Val Gly Lys
1               5                   10                  15

Ser Ala Leu Thr Ile Gln Leu Ile Gln Asn His Phe Val Asp Glu Tyr
                20                  25                  30

Asp Pro Thr Ile Glu Asp Ser Tyr Arg Lys Gln Val Val Ile Asp Gly
            35                  40                  45

Glu Thr Cys Leu Leu Asp Ile Leu Asp Thr Ala Gly Gln Glu Glu Tyr
    50                  55                  60

Ser Ala Met Arg Asp Gln Tyr Met Arg Thr Gly Glu Gly Phe Leu Cys
65                  70                  75                  80

Val Phe Ala Ile Asn Asn Thr Lys Ser Phe Glu Asp Ile His His Tyr
                85                  90                  95

Arg Glu Gln Ile Lys Arg Val Lys Asp Ser Glu Asp Val Pro Met Val
            100                 105                 110

Leu Val Gly Asn Lys Cys Asp Leu Pro Ser Arg Thr Val Asp Thr Lys
        115                 120                 125

Gln Ala Gln Asp Leu Ala Arg Ser Tyr Gly Ile Pro Phe Ile Glu Thr
    130                 135                 140

Ser Ala Lys Thr Arg Gln Gly Val Asp Asp Ala Phe Tyr Thr Leu Val
145                 150                 155                 160

Arg Glu Ile Arg Lys His Lys Glu Lys Met Ser Lys Asp Gly Lys Lys
                165                 170                 175

Lys Lys Lys Lys Ser Lys Thr Lys Cys Val Ile Met
            180                 185

<210> SEQ ID NO 3
<211> LENGTH: 189
<212> TYPE: PRT
<213> ORGANISM: Homo sapiens

<400> SEQUENCE: 3

Met Thr Glu Tyr Lys Leu Val Val Val Gly Ala Gly Gly Val Gly Lys
1               5                   10                  15

Ser Ala Leu Thr Ile Gln Leu Ile Gln Asn His Phe Val Asp Glu Tyr
                20                  25                  30

Asp Pro Thr Ile Glu Asp Ser Tyr Arg Lys Gln Val Val Ile Asp Gly
            35                  40                  45

Glu Thr Cys Leu Leu Asp Ile Leu Asp Thr Ala Gly Gln Glu Glu Tyr
    50                  55                  60

Ser Ala Met Arg Asp Gln Tyr Met Arg Thr Gly Glu Gly Phe Leu Cys
65                  70                  75                  80

Val Phe Ala Ile Asn Asn Thr Lys Ser Phe Glu Asp Ile His Gln Tyr
                85                  90                  95

Arg Glu Gln Ile Lys Arg Val Lys Asp Ser Asp Asp Val Pro Met Val
```

```
                    100                 105                 110
Leu Val Gly Asn Lys Cys Asp Leu Ala Ala Arg Thr Val Glu Ser Arg
            115                 120                 125

Gln Ala Gln Asp Leu Ala Arg Ser Tyr Gly Ile Pro Tyr Ile Glu Thr
        130                 135                 140

Ser Ala Lys Thr Arg Gln Gly Val Glu Asp Ala Phe Tyr Thr Leu Val
145                 150                 155                 160

Arg Glu Ile Arg Gln His Lys Leu Arg Lys Leu Asn Pro Pro Asp Glu
                165                 170                 175

Ser Gly Pro Gly Cys Met Ser Cys Lys Cys Val Leu Ser
            180                 185

<210> SEQ ID NO 4
<211> LENGTH: 189
<212> TYPE: PRT
<213> ORGANISM: Homo sapiens

<400> SEQUENCE: 4

Met Thr Glu Tyr Lys Leu Val Val Val Gly Ala Gly Gly Val Gly Lys
1               5                   10                  15

Ser Ala Leu Thr Ile Gln Leu Ile Gln Asn His Phe Val Asp Glu Tyr
            20                  25                  30

Asp Pro Thr Ile Glu Asp Ser Tyr Arg Lys Gln Val Val Ile Asp Gly
        35                  40                  45

Glu Thr Cys Leu Leu Asp Ile Leu Asp Thr Ala Gly Gln Glu Glu Tyr
    50                  55                  60

Ser Ala Met Arg Asp Gln Tyr Met Arg Thr Gly Glu Gly Phe Leu Cys
65                  70                  75                  80

Val Phe Ala Ile Asn Asn Ser Lys Ser Phe Ala Asp Ile Asn Leu Tyr
                85                  90                  95

Arg Glu Gln Ile Lys Arg Val Lys Asp Ser Asp Asp Val Pro Met Val
            100                 105                 110

Leu Val Gly Asn Lys Cys Asp Leu Pro Thr Arg Thr Val Asp Thr Lys
        115                 120                 125

Gln Ala His Glu Leu Ala Lys Ser Tyr Gly Ile Pro Phe Ile Glu Thr
    130                 135                 140

Ser Ala Lys Thr Arg Gln Gly Val Glu Asp Ala Phe Tyr Thr Leu Val
145                 150                 155                 160

Arg Glu Ile Arg Gln Tyr Arg Met Lys Lys Leu Asn Ser Ser Asp Asp
                165                 170                 175

Gly Thr Gln Gly Cys Met Gly Leu Pro Cys Val Val Met
            180                 185

<210> SEQ ID NO 5
<211> LENGTH: 11
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(1)
<223> OTHER INFORMATION: Xaa can be any naturally occurring amino acid
<220> FEATURE:
<221> NAME/KEY: misc_feature
<222> LOCATION: (7)..(8)
<223> OTHER INFORMATION: Xaa can be any naturally occurring amino acid
<220> FEATURE:
<221> NAME/KEY: misc_feature
<222> LOCATION: (10)..(11)
```

-continued

```
<223> OTHER INFORMATION: Xaa can be any naturally occurring amino acid

<400> SEQUENCE: 5

Xaa Tyr Thr Leu Val Arg Xaa Xaa Arg Xaa Xaa
1               5                   10

<210> SEQ ID NO 6
<211> LENGTH: 10
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (5)..(5)
<223> OTHER INFORMATION: Xaa can be any naturally occurring amino acid
      or norleucine.

<400> SEQUENCE: 6

Lys Thr Pro Gly Xaa Val Lys Ile Lys Lys
1               5                   10

<210> SEQ ID NO 7
<211> LENGTH: 6
<212> TYPE: PRT
<213> ORGANISM: Artificial Sequence
<220> FEATURE:
<223> OTHER INFORMATION: Synthetic

<400> SEQUENCE: 7

Lys Lys Ser Lys Thr Lys
1               5

<210> SEQ ID NO 8
<211> LENGTH: 9
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (5)..(6)
<223> OTHER INFORMATION: Xaa can be any naturally occurring amino acid
      or norleucine.
<220> FEATURE:
<221> NAME/KEY: MISC_FEATURE
<222> LOCATION: (8)..(9)
<223> OTHER INFORMATION: Xaa can be any naturally occurring amino acid
      or norleucine.

<400> SEQUENCE: 8

Ser Gly Pro Gly Xaa Xaa Ser Xaa Xaa
1               5

<210> SEQ ID NO 9
<211> LENGTH: 9
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (5)..(6)
<223> OTHER INFORMATION: Xaa can be any naturally occurring amino acid
      or norleucine.

<400> SEQUENCE: 9

Gly Thr Gln Gly Xaa Xaa Gly Leu Pro
1               5
```

```
<210> SEQ ID NO 10
<211> LENGTH: 16
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: Xaa is palmitoylated arginine.

<400> SEQUENCE: 10

Xaa Tyr Gln Arg Ile Glu Arg Val Leu Thr Tyr Phe Ala Asp Glu Val
1               5                   10                  15

<210> SEQ ID NO 11
<211> LENGTH: 17
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: Xaa is palmitoylated leucine.

<400> SEQUENCE: 11

Xaa Arg Tyr Gln Arg Ile Glu Arg Val Leu Thr Tyr Phe Ala Asp Glu
1               5                   10                  15

Val

<210> SEQ ID NO 12
<211> LENGTH: 17
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: Xaa is palmitoylated lysine.

<400> SEQUENCE: 12

Xaa Arg Tyr Gln Arg Ile Glu Arg Val Leu Thr Tyr Phe Ala Asp Glu
1               5                   10                  15

Val

<210> SEQ ID NO 13
<211> LENGTH: 17
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: Xaa is palmitoylated lysine.

<400> SEQUENCE: 13

Xaa Val Glu Asp Ala Phe Tyr Thr Leu Val Arg Glu Ile Arg Gln Tyr
1               5                   10                  15

Arg

<210> SEQ ID NO 14
<211> LENGTH: 17
<212> TYPE: PRT
<213> ORGANISM: Artificial Sequence
```

```
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: Xaa is acetylated 2-dodecyl-alanine.

<400> SEQUENCE: 14

Xaa Val Glu Asp Ala Phe Tyr Thr Leu Val Arg Glu Ile Arg Gln Tyr
1               5                   10                  15

Arg

<210> SEQ ID NO 15
<211> LENGTH: 14
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: Xaa is palmitoylated lysine.

<400> SEQUENCE: 15

Xaa Ala Phe Tyr Thr Leu Val Arg Glu Ile Arg Gln Tyr Arg
1               5                   10

<210> SEQ ID NO 16
<211> LENGTH: 17
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: Xaa is acetylated valine.
<220> FEATURE:
<221> NAME/KEY: MISC_FEATURE
<222> LOCATION: (17)..(17)
<223> OTHER INFORMATION: Xaa is palmiloylated lysine.

<400> SEQUENCE: 16

Xaa Glu Asp Ala Phe Tyr Thr Leu Val Arg Glu Ile Arg Gln Tyr Arg
1               5                   10                  15

Xaa

<210> SEQ ID NO 17
<211> LENGTH: 14
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: Xaa is acetylated alanine.
<220> FEATURE:
<221> NAME/KEY: MISC_FEATURE
<222> LOCATION: (14)..(14)
<223> OTHER INFORMATION: Xaa is palmitoylated lysine.

<400> SEQUENCE: 17

Xaa Phe Tyr Thr Leu Val Arg Glu Ile Arg Gln Tyr Arg Xaa
1               5                   10

<210> SEQ ID NO 18
<211> LENGTH: 15
<212> TYPE: PRT
```

```
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: Xaa is acetylated aspartic acid.
<220> FEATURE:
<221> NAME/KEY: MISC_FEATURE
<222> LOCATION: (15)..(15)
<223> OTHER INFORMATION: Xaa is palmitoylated lysine.

<400> SEQUENCE: 18

Xaa Ala Phe Tyr Thr Leu Val Arg Glu Ile Arg Gln Tyr Arg Xaa
1               5                   10                  15

<210> SEQ ID NO 19
<211> LENGTH: 13
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: Xaa is palmitoylated lysine.

<400> SEQUENCE: 19

Xaa Ala Phe Tyr Thr Leu Val Arg Glu Ile Arg Gln Tyr
1               5                   10

<210> SEQ ID NO 20
<211> LENGTH: 13
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: Xaa is palmitoylated lysine.

<400> SEQUENCE: 20

Xaa Phe Tyr Thr Leu Val Arg Glu Ile Arg Gln Tyr Arg
1               5                   10

<210> SEQ ID NO 21
<211> LENGTH: 12
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: Xaa is acetylated tyrosine.
<220> FEATURE:
<221> NAME/KEY: MISC_FEATURE
<222> LOCATION: (12)..(12)
<223> OTHER INFORMATION: Xaa is palmitoylated lysine.

<400> SEQUENCE: 21

Xaa Gln Arg Ile Gln Arg Val Leu Thr Tyr Phe Xaa
1               5                   10

<210> SEQ ID NO 22
<211> LENGTH: 12
<212> TYPE: PRT
<213> ORGANISM: Artificial Sequence
<220> FEATURE:
<223> OTHER INFORMATION: Synthetic
```

```
<220> FEATURE:
<221> NAME/KEY: MISC_FEATURE
<222> LOCATION: (1)..(1)
<223> OTHER INFORMATION: Xaa is acetylated tyrosine.
<220> FEATURE:
<221> NAME/KEY: MISC_FEATURE
<222> LOCATION: (12)..(12)
<223> OTHER INFORMATION: Xaa is palmitoylated lysine.

<400> SEQUENCE: 22

Xaa Gln Arg Lys Gln Arg Val Leu Thr Tyr Phe Xaa
1               5                   10

<210> SEQ ID NO 23
<211> LENGTH: 11
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: Xaa is palmitoylated tyrosine.

<400> SEQUENCE: 23

Xaa Gln Arg Lys Gln Arg Val Leu Thr Tyr Phe
1               5                   10

<210> SEQ ID NO 24
<211> LENGTH: 16
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: Xaa is acetylated valine.

<400> SEQUENCE: 24

Xaa Glu Asp Ala Phe Tyr Thr Leu Val Arg Glu Ile Arg Gln Tyr Arg
1               5                   10                  15

<210> SEQ ID NO 25
<211> LENGTH: 13
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: Xaa is acetylated alanine.

<400> SEQUENCE: 25

Xaa Phe Tyr Thr Leu Val Arg Glu Ile Arg Gln Tyr Arg
1               5                   10

<210> SEQ ID NO 26
<211> LENGTH: 14
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: Xaa is palmitoylated lysine.

<400> SEQUENCE: 26
```

Xaa Ala Phe Tyr Thr Leu Val Arg Glu Ile Arg Lys His Lys
1               5                   10

<210> SEQ ID NO 27
<211> LENGTH: 13
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: Xaa is palmitoylated arginine.

<400> SEQUENCE: 27

Xaa Tyr Gln Arg Ile Gln Arg Val Leu Thr Tyr Phe Ala
1               5                   10

<210> SEQ ID NO 28
<211> LENGTH: 12
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: Xaa is palmitoylated arginine.

<400> SEQUENCE: 28

Xaa Tyr Gln Arg Ile Gln Arg Val Leu Thr Tyr Phe
1               5                   10

<210> SEQ ID NO 29
<211> LENGTH: 12
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: Xaa is palmitoylated tyrosine.

<400> SEQUENCE: 29

Xaa Gln Arg Ile Gln Arg Val Leu Thr Tyr Phe Ala
1               5                   10

<210> SEQ ID NO 30
<211> LENGTH: 13
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: Xaa is palmitoylated arginine.

<400> SEQUENCE: 30

Xaa Tyr Gln Arg Val Gln Arg Val Leu Thr Tyr Phe Ala
1               5                   10

<210> SEQ ID NO 31
<211> LENGTH: 14
<212> TYPE: PRT
<213> ORGANISM: Artificial Sequence
<220> FEATURE:
<223> OTHER INFORMATION: Synthetic
<220> FEATURE:

```
<221> NAME/KEY: MISC_FEATURE
<222> LOCATION: (1)..(1)
<223> OTHER INFORMATION: Xaa is acetylated arginine.
<220> FEATURE:
<221> NAME/KEY: MISC_FEATURE
<222> LOCATION: (14)..(14)
<223> OTHER INFORMATION: Xaa is palmitoylated lysine.

<400> SEQUENCE: 31

Xaa Tyr Gln Arg Ile Glu Arg Val Leu Thr Tyr Phe Ala Xaa
1               5                   10

<210> SEQ ID NO 32
<211> LENGTH: 15
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: Xaa is palmitoylated lysine.

<400> SEQUENCE: 32

Xaa Ala Phe Tyr Thr Leu Val Arg Glu Ile Arg Gln Tyr Arg Leu
1               5                   10                  15

<210> SEQ ID NO 33
<211> LENGTH: 15
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: Xaa is palmitoylated lysine.

<400> SEQUENCE: 33

Xaa Ala Phe Tyr Thr Leu Val Arg Gln Ile Arg Gln Tyr Arg Leu
1               5                   10                  15

<210> SEQ ID NO 34
<211> LENGTH: 14
<212> TYPE: PRT
<213> ORGANISM: Artificial Sequence
<220> FEATURE:
<223> OTHER INFORMATION: synthetic
<220> FEATURE:
<221> NAME/KEY: MISC_FEATURE
<222> LOCATION: (1)..(1)
<223> OTHER INFORMATION: Xaa is acetylated arginine.
<220> FEATURE:
<221> NAME/KEY: MISC_FEATURE
<222> LOCATION: (14)..(14)
<223> OTHER INFORMATION: Xaa is palmitoylated lysine.

<400> SEQUENCE: 34

Xaa Tyr Gln Arg Ile Gln Arg Val Leu Thr Tyr Phe Ala Xaa
1               5                   10

<210> SEQ ID NO 35
<211> LENGTH: 15
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: Xaa is acetylated leucine.
```

```
<220> FEATURE:
<221> NAME/KEY: MISC_FEATURE
<222> LOCATION: (15)..(15)
<223> OTHER INFORMATION: Xaa is palmitoylated lysine.

<400> SEQUENCE: 35

Xaa Arg Tyr Gln Arg Ile Gln Arg Val Leu Thr Tyr Phe Ala Xaa
1               5                   10                  15

<210> SEQ ID NO 36
<211> LENGTH: 13
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: Xaa is acetylated arginine.
<220> FEATURE:
<221> NAME/KEY: MISC_FEATURE
<222> LOCATION: (13)..(13)
<223> OTHER INFORMATION: Xaa is palmitoylated lysine.

<400> SEQUENCE: 36

Xaa Tyr Gln Arg Ile Gln Arg Val Leu Thr Tyr Phe Xaa
1               5                   10

<210> SEQ ID NO 37
<211> LENGTH: 13
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: Xaa is acetylated tyrosine.
<220> FEATURE:
<221> NAME/KEY: MISC_FEATURE
<222> LOCATION: (13)..(13)
<223> OTHER INFORMATION: Xaa is palmitoylated lysine.

<400> SEQUENCE: 37

Xaa Gln Arg Ile Gln Arg Val Leu Thr Tyr Phe Ala Xaa
1               5                   10

<210> SEQ ID NO 38
<211> LENGTH: 11
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: Xaa is palmitoylated tyrosine.

<400> SEQUENCE: 38

Xaa Gln Arg Ile Gln Arg Val Leu Thr Tyr Phe
1               5                   10

<210> SEQ ID NO 39
<211> LENGTH: 12
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
```

<223> OTHER INFORMATION: Xaa is palmitoylated amino isobutiric acid

<400> SEQUENCE: 39

Xaa Tyr Gln Arg Ile Gln Arg Val Leu Thr Tyr Phe
1               5                   10

<210> SEQ ID NO 40
<211> LENGTH: 11
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: Xaa is palmitoylated tyrosine.

<400> SEQUENCE: 40

Xaa Gln Arg Val Gln Arg Val Leu Thr Tyr Phe
1               5                   10

<210> SEQ ID NO 41
<211> LENGTH: 11
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: Xaa is lauric acid-bound tyrosine.

<400> SEQUENCE: 41

Xaa Gln Arg Val Gln Arg Val Leu Thr Tyr Phe
1               5                   10

<210> SEQ ID NO 42
<211> LENGTH: 11
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: Xaa is lauric acid-bound tyrosine.

<400> SEQUENCE: 42

Xaa Gln Arg Val Gln Arg Val Leu Thr Tyr Trp
1               5                   10

<210> SEQ ID NO 43
<211> LENGTH: 11
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: Xaa is myristic acid-bound tyrosine.

<400> SEQUENCE: 43

Xaa Gln Arg Val Gln Arg Val Leu Thr Tyr Trp
1               5                   10

<210> SEQ ID NO 44
<211> LENGTH: 11
<212> TYPE: PRT

```
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: Xaa is caprylic acid-bound tyrosine.

<400> SEQUENCE: 44

Xaa Gln Arg Val Gln Arg Val Leu Thr Tyr Trp
1               5                   10

<210> SEQ ID NO 45
<211> LENGTH: 11
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: Xaa is lauric acid-bound tyrosine.

<400> SEQUENCE: 45

Xaa Lys Arg Val Gln Arg Val Leu Thr Tyr Phe
1               5                   10

<210> SEQ ID NO 46
<211> LENGTH: 11
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: Xaa is lauric acid-bound histidine.

<400> SEQUENCE: 46

Xaa Gln Arg Val Gln Arg Val Leu Thr Tyr Phe
1               5                   10

<210> SEQ ID NO 47
<211> LENGTH: 20
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: Xaa is acetylated arginine.
<220> FEATURE:
<221> NAME/KEY: MISC_FEATURE
<222> LOCATION: (20)..(20)
<223> OTHER INFORMATION: Xaa is palmitoylated lysine.

<400> SEQUENCE: 47

Xaa Leu Lys Lys Ile Ser Lys Glu Glu Lys Thr Pro Gly Ser Val Lys
1               5                   10                  15

Ile Lys Lys Xaa
            20

<210> SEQ ID NO 48
<211> LENGTH: 15
<212> TYPE: PRT
<213> ORGANISM: Artificial Sequence
<220> FEATURE:
<223> OTHER INFORMATION: Synthetic
<220> FEATURE:
```

<221> NAME/KEY: MISC_FEATURE
<222> LOCATION: (1)..(1)
<223> OTHER INFORMATION: Xaa is acetylated tyrosine.
<220> FEATURE:
<221> NAME/KEY: MISC_FEATURE
<222> LOCATION: (15)..(15)
<223> OTHER INFORMATION: Xaa is palmitoylated lysine.

<400> SEQUENCE: 48

Xaa Arg Leu Lys Lys Ile Ser Lys Glu Glu Lys Thr Pro Gly Xaa
1               5                   10                  15

<210> SEQ ID NO 49
<211> LENGTH: 11
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: Xaa is acetylated lysine.
<220> FEATURE:
<221> NAME/KEY: MISC_FEATURE
<222> LOCATION: (5)..(5)
<223> OTHER INFORMATION: Xaa is norleucine.
<220> FEATURE:
<221> NAME/KEY: MISC_FEATURE
<222> LOCATION: (11)..(11)
<223> OTHER INFORMATION: Xaa is palmitoylated lysine.

<400> SEQUENCE: 49

Xaa Thr Pro Gly Xaa Val Lys Ile Lys Lys Xaa
1               5                   10

<210> SEQ ID NO 50
<211> LENGTH: 20
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: Xaa is acetylated lysine.
<220> FEATURE:
<221> NAME/KEY: MISC_FEATURE
<222> LOCATION: (14)..(14)
<223> OTHER INFORMATION: Xaa is norleucine.
<220> FEATURE:
<221> NAME/KEY: MISC_FEATURE
<222> LOCATION: (20)..(20)
<223> OTHER INFORMATION: Xaa is palmitoylated lysine.

<400> SEQUENCE: 50

Xaa Leu Lys Lys Ile Ser Lys Glu Glu Lys Thr Pro Gly Xaa Val Lys
1               5                   10                  15

Ile Lys Lys Xaa
            20

<210> SEQ ID NO 51
<211> LENGTH: 11
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: Xaa is acetylated lysine.
<220> FEATURE:
<221> NAME/KEY: MISC_FEATURE

```
<222> LOCATION: (11)..(11)
<223> OTHER INFORMATION: Xaa is palmitoylated lysine.

<400> SEQUENCE: 51

Xaa Thr Pro Gly Ala Val Lys Ile Lys Lys Xaa
1               5                   10

<210> SEQ ID NO 52
<211> LENGTH: 10
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: Xaa is acetylated tyrosine.
<220> FEATURE:
<221> NAME/KEY: MISC_FEATURE
<222> LOCATION: (4)..(4)
<223> OTHER INFORMATION: Xaa is norleucine.
<220> FEATURE:
<221> NAME/KEY: MISC_FEATURE
<222> LOCATION: (10)..(10)
<223> OTHER INFORMATION: Xaa is palmitoylated lysine.

<400> SEQUENCE: 52

Xaa Pro Gly Xaa Val Lys Ile Lys Lys Xaa
1               5                   10

<210> SEQ ID NO 53
<211> LENGTH: 9
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: Xaa is acetylated proline.
<220> FEATURE:
<221> NAME/KEY: MISC_FEATURE
<222> LOCATION: (3)..(3)
<223> OTHER INFORMATION: Xaa is norleucine.
<220> FEATURE:
<221> NAME/KEY: MISC_FEATURE
<222> LOCATION: (9)..(9)
<223> OTHER INFORMATION: Xaa is palmitoylated lysine.

<400> SEQUENCE: 53

Xaa Gly Xaa Val Lys Ile Lys Lys Xaa
1               5

<210> SEQ ID NO 54
<211> LENGTH: 8
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: Xaa is acetylated glycine.
<220> FEATURE:
<221> NAME/KEY: MISC_FEATURE
<222> LOCATION: (2)..(2)
<223> OTHER INFORMATION: Xaa is norleucine.
<220> FEATURE:
<221> NAME/KEY: MISC_FEATURE
<222> LOCATION: (8)..(8)
<223> OTHER INFORMATION: Xaa is palmitoylated lysine.

<400> SEQUENCE: 54
```

```
Xaa Xaa Val Lys Ile Lys Lys Xaa
1               5
```

```
<210> SEQ ID NO 55
<211> LENGTH: 19
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: Xaa is acetylated lysine.
<220> FEATURE:
<221> NAME/KEY: MISC_FEATURE
<222> LOCATION: (4)..(4)
<223> OTHER INFORMATION: Xaa is norleucine.
<220> FEATURE:
<221> NAME/KEY: MISC_FEATURE
<222> LOCATION: (19)..(19)
<223> OTHER INFORMATION: Xaa is palmitoylated lysine.

<400> SEQUENCE: 55

Xaa Glu Lys Xaa Ser Lys Asp Gly Lys Lys Lys Lys Lys Ser Lys
1               5                   10                  15

Thr Lys Xaa
```

```
<210> SEQ ID NO 56
<211> LENGTH: 17
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: Xaa is acetylated lycine.
<220> FEATURE:
<221> NAME/KEY: MISC_FEATURE
<222> LOCATION: (2)..(2)
<223> OTHER INFORMATION: Xaa is norleucine.
<220> FEATURE:
<221> NAME/KEY: MISC_FEATURE
<222> LOCATION: (17)..(17)
<223> OTHER INFORMATION: Xaa is palmitoylated lysine.

<400> SEQUENCE: 56

Xaa Xaa Ser Lys Asp Gly Lys Lys Lys Lys Ser Lys Thr Lys
1               5                   10                  15

Xaa
```

```
<210> SEQ ID NO 57
<211> LENGTH: 11
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: Xaa is acetylated lysine.
<220> FEATURE:
<221> NAME/KEY: MISC_FEATURE
<222> LOCATION: (11)..(11)
<223> OTHER INFORMATION: Xaa is palmitoylated lysine.

<400> SEQUENCE: 57

Xaa Lys Lys Lys Lys Lys Ser Lys Thr Lys Xaa
1               5                   10
```

```
<210> SEQ ID NO 58
<211> LENGTH: 10
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: Xaa is acetylated lysine.
<220> FEATURE:
<221> NAME/KEY: MISC_FEATURE
<222> LOCATION: (10)..(10)
<223> OTHER INFORMATION: Xaa is palmitoylated lysine.

<400> SEQUENCE: 58

Xaa Lys Lys Lys Lys Ser Lys Thr Lys Xaa
1               5                   10

<210> SEQ ID NO 59
<211> LENGTH: 9
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: Xaa is palmitoylated lysine.

<400> SEQUENCE: 59

Xaa Thr Lys Ser Lys Lys Lys Lys Lys
1               5

<210> SEQ ID NO 60
<211> LENGTH: 10
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: Xaa is palmitoylated lysine.

<400> SEQUENCE: 60

Xaa Lys Thr Lys Ser Lys Lys Lys Lys Lys
1               5                   10

<210> SEQ ID NO 61
<211> LENGTH: 9
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: Xaa is acetylated lysine.
<220> FEATURE:
<221> NAME/KEY: MISC_FEATURE
<222> LOCATION: (9)..(9)
<223> OTHER INFORMATION: Xaa is palmitoylated lysine.

<400> SEQUENCE: 61

Xaa Lys Lys Lys Ser Lys Thr Lys Xaa
1               5

<210> SEQ ID NO 62
<211> LENGTH: 8
```

```
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: Xaa is acetylated lysine.
<220> FEATURE:
<221> NAME/KEY: MISC_FEATURE
<222> LOCATION: (8)..(8)
<223> OTHER INFORMATION: Xaa is palmitoylated lysine.

<400> SEQUENCE: 62

Xaa Lys Lys Ser Lys Thr Lys Xaa
1               5

<210> SEQ ID NO 63
<211> LENGTH: 7
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: Xaa is acetylated lysine.
<220> FEATURE:
<221> NAME/KEY: MISC_FEATURE
<222> LOCATION: (7)..(7)
<223> OTHER INFORMATION: Xaa is palmitoylated lysine.

<400> SEQUENCE: 63

Xaa Lys Ser Lys Thr Lys Xaa
1               5

<210> SEQ ID NO 64
<211> LENGTH: 11
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: Xaa is acetylated glutamic acid.
<220> FEATURE:
<221> NAME/KEY: MISC_FEATURE
<222> LOCATION: (6)..(7)
<223> OTHER INFORMATION: Xaa is norleucine.
<220> FEATURE:
<221> NAME/KEY: MISC_FEATURE
<222> LOCATION: (9)..(9)
<223> OTHER INFORMATION: Xaa is norleucine.
<220> FEATURE:
<221> NAME/KEY: MISC_FEATURE
<222> LOCATION: (11)..(11)
<223> OTHER INFORMATION: Xaa is palmitoylated lysine.

<400> SEQUENCE: 64

Xaa Ser Gly Pro Gly Xaa Xaa Ser Xaa Lys Xaa
1               5                   10

<210> SEQ ID NO 65
<211> LENGTH: 11
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: Xaa is acetylated aspartic acid.
```

```
<220> FEATURE:
<221> NAME/KEY: MISC_FEATURE
<222> LOCATION: (6)..(7)
<223> OTHER INFORMATION: Xaa is norleucine.
<220> FEATURE:
<221> NAME/KEY: MISC_FEATURE
<222> LOCATION: (11)..(11)
<223> OTHER INFORMATION: Xaa is palmitoylated lysine.

<400> SEQUENCE: 65

Xaa Gly Thr Gln Gly Xaa Xaa Gly Leu Pro Xaa
1               5                   10

<210> SEQ ID NO 66
<211> LENGTH: 12
<212> TYPE: PRT
<213> ORGANISM: Artificial Sequence
<220> FEATURE:
<223> OTHER INFORMATION: Synthetic

<400> SEQUENCE: 66

Ala Phe Tyr Thr Leu Val Arg Glu Ile Arg Gln Tyr
1               5                   10

<210> SEQ ID NO 67
<211> LENGTH: 12
<212> TYPE: PRT
<213> ORGANISM: Artificial Sequence
<220> FEATURE:
<223> OTHER INFORMATION: Synthetic

<400> SEQUENCE: 67

Ala Phe Tyr Thr Leu Val Arg Glu Ile Arg Lys His
1               5                   10

<210> SEQ ID NO 68
<211> LENGTH: 12
<212> TYPE: PRT
<213> ORGANISM: Artificial Sequence
<220> FEATURE:
<223> OTHER INFORMATION: Synthetic

<400> SEQUENCE: 68

Ala Phe Tyr Thr Leu Val Arg Glu Ile Arg Gln His
1               5                   10

<210> SEQ ID NO 69
<211> LENGTH: 9
<212> TYPE: PRT
<213> ORGANISM: Artificial Sequence
<220> FEATURE:
<223> OTHER INFORMATION: Synthetic

<400> SEQUENCE: 69

Thr Pro Gly Cys Val Lys Ile Lys Lys
1               5

<210> SEQ ID NO 70
<211> LENGTH: 9
<212> TYPE: PRT
<213> ORGANISM: Artificial Sequence
<220> FEATURE:
<223> OTHER INFORMATION: Synthetic

<400> SEQUENCE: 70

Lys Lys Lys Lys Lys Ser Lys Thr Lys
1               5
```

<210> SEQ ID NO 71
<211> LENGTH: 9
<212> TYPE: PRT
<213> ORGANISM: Artificial Sequence
<220> FEATURE:
<223> OTHER INFORMATION: Synthetic

<400> SEQUENCE: 71

Ser Gly Pro Gly Cys Met Ser Cys Lys
1               5

<210> SEQ ID NO 72
<211> LENGTH: 9
<212> TYPE: PRT
<213> ORGANISM: Artificial Sequence
<220> FEATURE:
<223> OTHER INFORMATION: Synthetic

<400> SEQUENCE: 72

Gly Thr Gln Gly Cys Met Gly Leu Pro
1               5

<210> SEQ ID NO 73
<211> LENGTH: 4
<212> TYPE: PRT
<213> ORGANISM: Artificial Sequence
<220> FEATURE:
<223> OTHER INFORMATION: Synthetic

<400> SEQUENCE: 73

Arg Gln Ile Lys
1

<210> SEQ ID NO 74
<211> LENGTH: 4
<212> TYPE: PRT
<213> ORGANISM: Artificial Sequence
<220> FEATURE:
<223> OTHER INFORMATION: Synthetic

<400> SEQUENCE: 74

Lys Gln Ile Lys
1

<210> SEQ ID NO 75
<211> LENGTH: 11
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: Xaa is lauric acid-bound tryptophan.

<400> SEQUENCE: 75

Xaa Gln Arg Val Gln Arg Val Leu Thr Tyr Phe
1               5                   10

<210> SEQ ID NO 76
<211> LENGTH: 12
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)

```
<223> OTHER INFORMATION: Xaa is lauric acid-bound tyrosine.

<400> SEQUENCE: 76

Xaa Gln Arg Val Gln Arg Val Leu Thr Tyr Phe Cys
1               5                   10

<210> SEQ ID NO 77
<211> LENGTH: 12
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: Xaa is acetylated tyrosine.

<400> SEQUENCE: 77

Xaa Gln Arg Val Gln Arg Val Leu Thr Tyr Phe Cys
1               5                   10

<210> SEQ ID NO 78
<211> LENGTH: 12
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: Xaa is lauric acid-bound tyrosine.

<400> SEQUENCE: 78

Xaa Gln Arg Val Gln Arg Val Leu Thr Tyr Phe Ala
1               5                   10

<210> SEQ ID NO 79
<211> LENGTH: 12
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: Xaa is caprylic acid-bound tyrosine.

<400> SEQUENCE: 79

Xaa Gln Arg Val Gln Arg Val Leu Thr Tyr Phe Ala
1               5                   10

<210> SEQ ID NO 80
<211> LENGTH: 11
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: Xaa is caprylic acid-bound tyrosine.

<400> SEQUENCE: 80

Xaa Gln Arg Val Gln Arg Val Leu Thr Tyr Phe
1               5                   10

<210> SEQ ID NO 81
<211> LENGTH: 11
<212> TYPE: PRT
```

```
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: Xaa is octanoic acid-bound tyrosine.

<400> SEQUENCE: 81

Xaa Gln Arg Val Gln Arg Val Leu Thr Tyr Phe
1               5                   10

<210> SEQ ID NO 82
<211> LENGTH: 12
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: Xaa is lauric acid-bound tyrosine.

<400> SEQUENCE: 82

Xaa Gln Arg Val Gln Arg Val Leu Thr Tyr Phe Cys
1               5                   10

<210> SEQ ID NO 83
<211> LENGTH: 12
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: Xaa is octanoic acid-bound tyrosine.

<400> SEQUENCE: 83

Xaa Gln Arg Val Gln Arg Val Leu Thr Tyr Phe Ala
1               5                   10

<210> SEQ ID NO 84
<211> LENGTH: 12
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: Xaa is octanoic acid-bound tryptophan.

<400> SEQUENCE: 84

Xaa Gln Arg Val Gln Arg Val Leu Thr Tyr Phe Ala
1               5                   10

<210> SEQ ID NO 85
<211> LENGTH: 10
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: Xaa is palmitoylated lysine.
<220> FEATURE:
<221> NAME/KEY: MISC_FEATURE
<222> LOCATION: (2)..(3)
<223> OTHER INFORMATION: Xaa is norleucine.
```

```
<220> FEATURE:
<221> NAME/KEY: MISC_FEATURE
<222> LOCATION: (5)..(5)
<223> OTHER INFORMATION: Xaa is norleucine.

<400> SEQUENCE: 85

Xaa Xaa Xaa Ser Xaa Gly Pro Gly Ser Glu
1               5                   10

<210> SEQ ID NO 86
<211> LENGTH: 10
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: Xaa is lauric acid-bound lysine.
<220> FEATURE:
<221> NAME/KEY: MISC_FEATURE
<222> LOCATION: (2)..(3)
<223> OTHER INFORMATION: Xaa is norleucine.
<220> FEATURE:
<221> NAME/KEY: MISC_FEATURE
<222> LOCATION: (5)..(5)
<223> OTHER INFORMATION: Xaa is norleucine.

<400> SEQUENCE: 86

Xaa Xaa Xaa Ser Xaa Gly Pro Gly Ser Glu
1               5                   10

<210> SEQ ID NO 87
<211> LENGTH: 14
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: Xaa is palmitoylated lysine.
<220> FEATURE:
<221> NAME/KEY: MISC_FEATURE
<222> LOCATION: (2)..(2)
<223> OTHER INFORMATION: Xaa is fluorescein-bound cysteine.

<400> SEQUENCE: 87

Xaa Xaa Phe Tyr Thr Leu Val Arg Glu Ile Arg Gln Tyr Arg
1               5                   10

<210> SEQ ID NO 88
<211> LENGTH: 13
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: Xaa is acetylated fluorescein-bound cysteine.

<400> SEQUENCE: 88

Xaa Phe Tyr Thr Leu Val Arg Glu Ile Arg Gln Tyr Arg
1               5                   10

<210> SEQ ID NO 89
<211> LENGTH: 11
<212> TYPE: PRT
<213> ORGANISM: Artificial Sequence
<220> FEATURE:
```

```
<223> OTHER INFORMATION: Synthetic
<220> FEATURE:
<221> NAME/KEY: MISC_FEATURE
<222> LOCATION: (1)..(1)
<223> OTHER INFORMATION: Xaa is acetylated fluorescein-bound cysteine.
<220> FEATURE:
<221> NAME/KEY: MISC_FEATURE
<222> LOCATION: (11)..(11)
<223> OTHER INFORMATION: Xaa is palmitoylated lysine.

<400> SEQUENCE: 89

Xaa Lys Lys Lys Lys Lys Ser Lys Thr Lys Xaa
1               5                   10

<210> SEQ ID NO 90
<211> LENGTH: 12
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: Xaa is acetylated fluorescein-bound cysteine.
<220> FEATURE:
<221> NAME/KEY: MISC_FEATURE
<222> LOCATION: (6)..(6)
<223> OTHER INFORMATION: Xaa is norleucine.
<220> FEATURE:
<221> NAME/KEY: MISC_FEATURE
<222> LOCATION: (12)..(12)
<223> OTHER INFORMATION: Xaa is palmitoylated lysine.

<400> SEQUENCE: 90

Xaa Lys Thr Pro Gly Xaa Val Lys Ile Lys Lys Xaa
1               5                   10

<210> SEQ ID NO 91
<211> LENGTH: 12
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: Xaa is acetylated fluorescein-bound cysteine.
<220> FEATURE:
<221> NAME/KEY: MISC_FEATURE
<222> LOCATION: (7)..(8)
<223> OTHER INFORMATION: Xaa is norleucine.
<220> FEATURE:
<221> NAME/KEY: MISC_FEATURE
<222> LOCATION: (10)..(10)
<223> OTHER INFORMATION: Xaa is norleucine.
<220> FEATURE:
<221> NAME/KEY: MISC_FEATURE
<222> LOCATION: (12)..(12)
<223> OTHER INFORMATION: Xaa is palmitoylated lysine.

<400> SEQUENCE: 91

Xaa Glu Ser Gly Pro Gly Xaa Xaa Ser Xaa Lys Xaa
1               5                   10
```